United States Patent
Bleau et al.

(10) Patent No.: US 10,675,167 B2
(45) Date of Patent: Jun. 9, 2020

(54) KNEE ORTHOSIS WITH HELICOIDAL AXIS AND METHOD OF DESIGN AND FABRICATION THEREOF

(71) Applicant: 2330-2029 QUÉBEC INC, Montréal, Québec (CA)

(72) Inventors: Jacinte Bleau, Boucherville (CA); Sébastien Hinse, Montréal (CA); Maxime Labelle, Longueuil (CA)

(73) Assignee: 2330-2029 QUÉBEC INC, Montréal, Québec (CA)

( * ) Notice: Subject to any disclaimer, the term of this patent is extended or adjusted under 35 U.S.C. 154(b) by 0 days.

(21) Appl. No.: 16/475,235

(22) PCT Filed: Dec. 4, 2018

(86) PCT No.: PCT/CA2018/051550
§ 371 (c)(1),
(2) Date: Jul. 1, 2019

(87) PCT Pub. No.: WO2019/109178
PCT Pub. Date: Jun. 13, 2019

(65) Prior Publication Data
US 2019/0328567 A1    Oct. 31, 2019

Related U.S. Application Data

(60) Provisional application No. 62/595,654, filed on Dec. 7, 2017.

(51) Int. Cl.
*A61F 5/01* (2006.01)
*G06F 30/00* (2020.01)
*A61B 5/00* (2006.01)

(52) U.S. Cl.
CPC ........... *A61F 5/0123* (2013.01); *G06F 30/00* (2020.01); *A61B 5/4585* (2013.01);
(Continued)

(58) Field of Classification Search
CPC ........... A61B 5/4585; A61F 2005/0146; A61F 2005/0148; A61F 2005/0151;
(Continued)

(56) References Cited

U.S. PATENT DOCUMENTS

| | | |
|---|---|---|
| 4,723,539 A | 2/1988 | Townsend |
| 5,230,696 A | 7/1993 | Silver et al. |

(Continued)

FOREIGN PATENT DOCUMENTS

| | | |
|---|---|---|
| CA | 2587410 C | 1/2015 |
| EP | 0361405 B1 | 12/1997 |

(Continued)

OTHER PUBLICATIONS

Aissaoui, R. et al., Robust estimation of screw axis from 3D pose using dual quaternion algebra, Ninth International Symposium on the 3D Analysis of Human Movement, 2006, Valenciennes (France), 28, 30.

(Continued)

*Primary Examiner* — Alireza Nia
*Assistant Examiner* — Caitlin A Carreiro
(74) *Attorney, Agent, or Firm* — Adsero IP

(57) ABSTRACT

A knee orthosis is provided. In described embodiments, the knee orthosis is designed to follow a natural movement of a wearer's knee along an asymmetric helicoidal axis of rotation. In some embodiments, the knee orthosis has hinges with shells having displacing geometric centers which do not coincide. In some embodiments, the knee orthosis is made of femoral and tibial hinges manufactured as single integral pieces. In some embodiments, the orthosis is configured to realign the wearer's knee in a frontal plane. Corresponding methods for designing and manufacturing a custom knee orthosis are also provided.

32 Claims, 25 Drawing Sheets

(52) U.S. Cl.
CPC .......... *A61F 2005/0165* (2013.01); *A61F 2005/0172* (2013.01); *A61H 2201/165* (2013.01); *A61H 2205/102* (2013.01); *G06T 2210/41* (2013.01)

(58) Field of Classification Search
CPC ...... A61F 2005/0165; A61F 2005/0172; A61F 5/0123; A61H 2201/165; A61H 2205/102; G06T 2210/41; G06F 30/00
USPC .............. 602/16, 23, 26, 62; 623/39–44
See application file for complete search history.

(56) References Cited

U.S. PATENT DOCUMENTS

| | | | |
|---|---|---|---|
| 5,792,086 | A | 8/1998 | Bleau et al. |
| 7,201,728 | B2 | 4/2007 | Sterling |
| 7,435,234 | B2 | 10/2008 | Gamada |
| 8,005,651 | B2 | 8/2011 | Summit et al. |
| 8,043,243 | B2 * | 10/2011 | Nathanson ........... A61F 5/0123 602/23 |
| 9,201,988 | B2 | 12/2015 | Stanhope et al. |
| 2004/0002674 | A1 | 1/2004 | Sterling |
| 2009/0240181 | A1 | 9/2009 | Sreeramagiri et al. |
| 2010/0222727 | A1 | 9/2010 | Naegerl |
| 2010/0268135 | A1 | 10/2010 | Summit et al. |
| 2010/0268138 | A1 | 10/2010 | Summit et al. |
| 2011/0004335 | A1 | 1/2011 | Summit et al. |
| 2015/0161299 | A1 | 6/2015 | Summit et al. |
| 2015/0328016 | A1 | 11/2015 | Summit et al. |

FOREIGN PATENT DOCUMENTS

| | | |
|---|---|---|
| EP | 1679052 B1 | 8/2009 |
| EP | 2699208 B1 | 5/2015 |
| WO | WO-2005-06782 A2 | 7/2005 |
| WO | WO-2011-057177 A1 | 5/2011 |
| WO | WO-2013-113909 A1 | 8/2013 |

OTHER PUBLICATIONS

Niesche, A. et al., Numerical evaluation and comparison of instantaneous anatomical knee joint axes and orthotic joint axes using MRI data under weight-bearing condition, European Conference of the International Federation for Medical and Biological Engineering 2008, IFMBE Proceedings 22, pp. 522-525, 2008.

Spoor, C. W. et al., Rigid body motion calculated from spatial co-ordinates of markers, Journal of Biomechanics, 13(4) pp. 391-393, 1980.

Woltring, H. J. et al., Finite centroid and helical axis estimation from noisy landmark measurements in the study of human joint kinematics, Journal of Biomechanics, 18(5), pp. 379-389, 1985.

Zeighami, A. et al., Tibio-femoral joint contact in healthy and osteoarthritic knees during quasi-static squat: A bi-planar X-ray analysis, Journal of Biomechanics, 2017, http://dx.doi.org/10.1016/j.jbiomech.2017.01.015.

International Search Report and Written Opinion dated Mar. 4, 2019, International Searching Authority for PCT International Patent Application No. PCT/CA2018/051550 filed on Dec. 4, 2018; 12 pages.

* cited by examiner

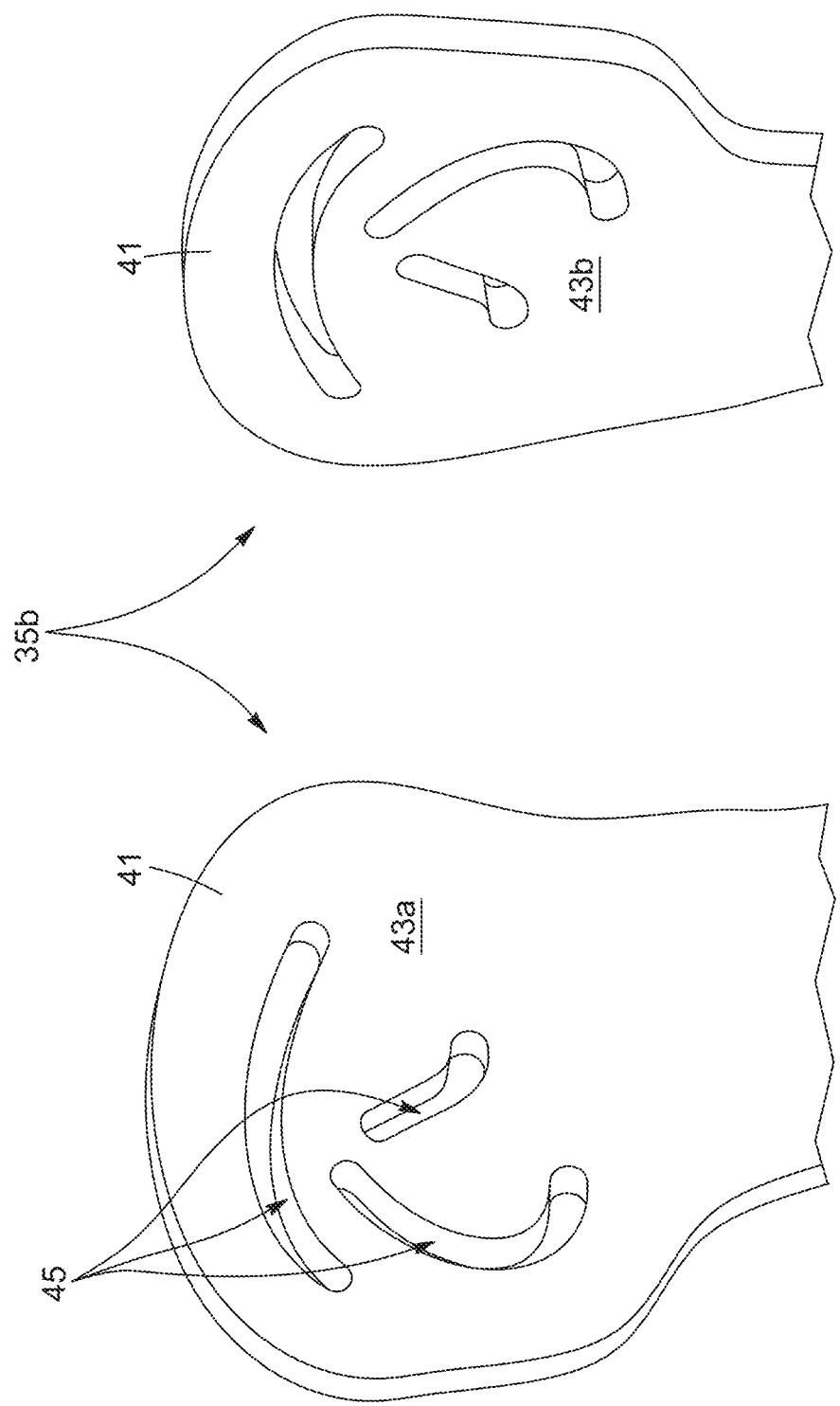

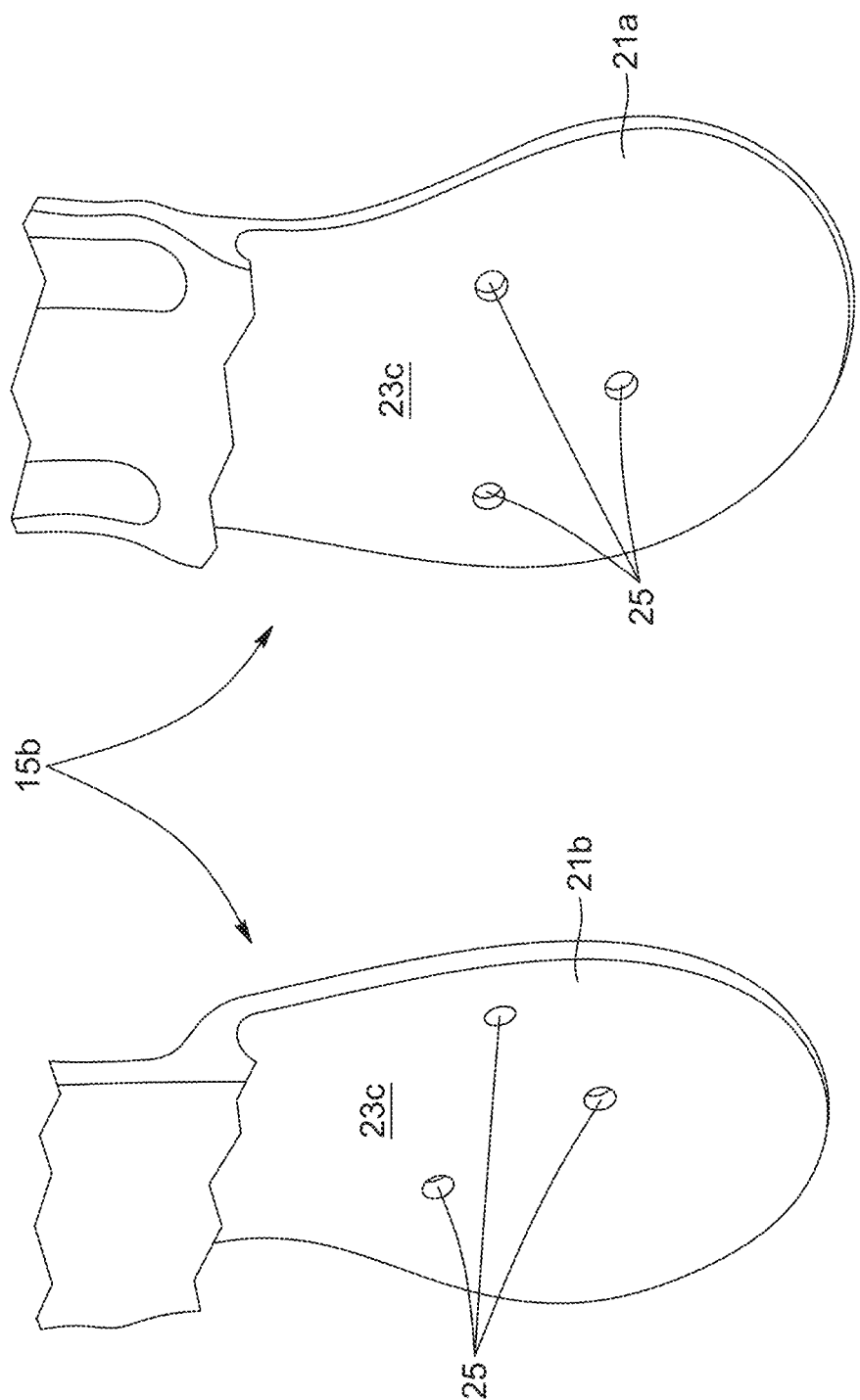

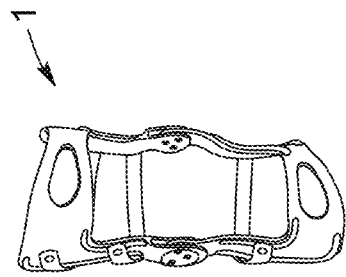
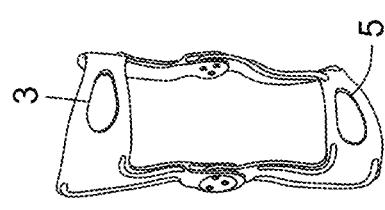
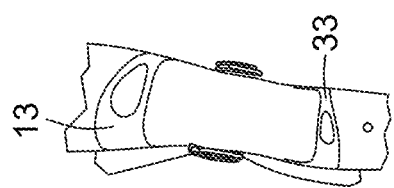
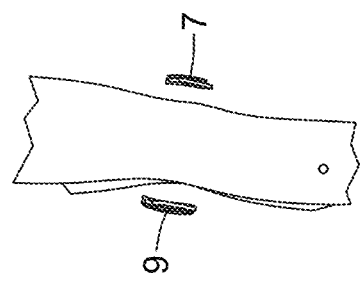
FIG. 25A  FIG. 25B  FIG. 25C  FIG. 25D
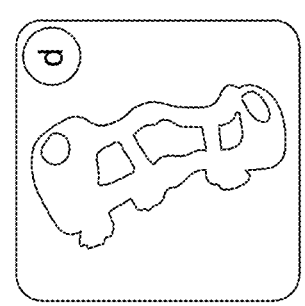
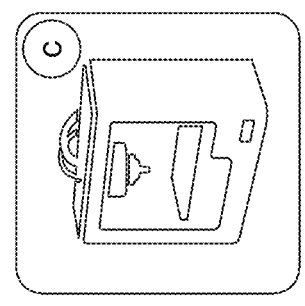
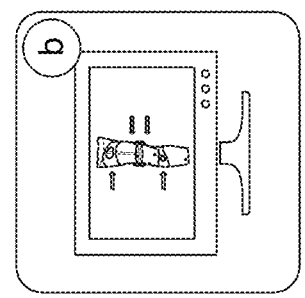
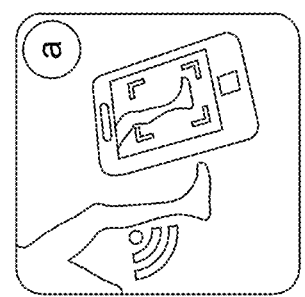
FIG. 26

KNEE ORTHOSIS WITH HELICOIDAL AXIS AND METHOD OF DESIGN AND FABRICATION THEREOF

RELATED APPLICATIONS

This application is a 35 U.S.C. § 371 national phase application of PCT/CA2018/051550 (WO-2019-109178-A1) filed on Dec. 4, 2018, entitled " KNEE ORTHOSIS WITH HELICOIDAL AXIS AND METHOD OF DESIGN AND FABRICATION THEREOF", which is a PCT application of U.S. 62/595,654 filed on Dec. 7, 2017, which is incorporated herein by reference in its entirety.

BACKGROUND

A knee orthosis is a device which is used to stabilize a wearer's knee after ligament instabilities, osteoarthritis, trauma or surgeries. Some existing orthoses are designed to account for a roll back femoral action, however such orthoses only work in the sagittal plane and do not fully account for the natural movement of the wearer's knee. There is thus much room for improvement.

SUMMARY

According to an aspect, a knee orthosis is provided. The knee orthosis includes: a femoral section for engaging relative to a wearer's femur; a tibial section for engaging relative to the wearer's tibia; a medial hinge pivotally engaging the femoral and tibial sections medial relative to the wearer's knee, the medial hinge comprising superposed shells having a shape corresponding to an arc of a sphere and having a first geometric center which displaces as the medial hinge is articulated; and a lateral hinge pivotally engaging the femoral and tibial sections lateral relative to the wearer's knee, the lateral hinge comprising superposed spherical shells having a shape corresponding to an arc of a sphere and having a second geometric center which displaces as the medial lateral hinge is articulated, the second geometric center displacing independent from the first geometric center; wherein the first and second geometric centers do not coincide with one another throughout a full articulation of the knee orthosis about the medial and lateral hinges.

According to an aspect, a knee orthosis is provided. The knee orthosis includes: a femoral section comprising a femoral cuff and a femoral hinge integrally formed as part of a single piece; and a tibial section comprising a tibial cuff and a tibial hinge, said tibial cuff and tibial hinge being integrally formed as part of a single piece; the femoral hinge and the tibial hinge being pivotally engaged to define an orthosis articulation allowing the femoral section and the tibial section to pivot relative to one another about a pivot axis, said pivot axis being configured to move in a sagittal plane, a frontal plane and a transverse plane, as the femoral and tibial sections are pivoted relative to one another about the articulation.

According to an aspect, an orthosis is provided. The orthosis includes: a proximal section for securing to a proximal portion of a wearer's limb, the proximal section comprising a proximal cuff and a proximal hinge integrally formed as part of a single piece; and a distal section for securing to a distal portion of the wearer's limb, the distal section being hingedly engageable with the proximal section, the distal section comprising a distal cuff and a distal hinge for engaging with the proximal hinge, said distal cuff and distal hinge being integrally formed as part of a single piece, the proximal hinge and the distal hinge together defining an orthosis articulation pivotable about a helicoidal hinge axis.

According to an aspect, a knee orthosis kit is provided. The knee orthosis kit includes: a femoral section comprising a femoral cuff and a femoral hinge integrally formed as part of a single piece; and a tibial section comprising a tibial cuff and a tibial hinge engaged with the femoral hinge, said tibial cuff and tibial hinge being integrally formed as part of a single piece, wherein the femoral section and the tibial section are securable to one another along the femoral and tibial hinge to form a knee orthosis articulable about a helicoidal hinge axis.

According to an aspect, a method for manufacturing a knee orthosis is provided. The method includes the steps of: a) obtaining a 3D model of a wearer's leg; b) virtually positioning medial and lateral hinges on medial and lateral femoral condyles using the 3D model; c) customizing the medial and lateral hinges to define an orthosis articulation which follows a natural movement of the wearer's knee; d) modelling femoral and tibial cuffs to conform to external surfaces of the 3D model; e) manufacturing a femoral section as a single piece comprising the femoral cuff and a femoral portion of the lateral and medial hinges; f) manufacturing a tibial section as a single piece comprising the tibial cuff and a tibial portion of the lateral and medial hinges; g) assembling the femoral and tibial sections to form the knee orthosis.

BRIEF DESCRIPTION OF THE DRAWINGS

FIG. 15A is a detail view of a tibial portion of a lateral hinge, according to an embodiment, showing an interior surface thereof; FIG. 15B is a detail view showing an exterior surface of the tibial portion of the lateral hinge of FIG. 15A;

FIG. 15C is a detail view showing an interior surface of a femoral portion of the lateral hinge, according to an embodiment; and FIG. 15D is a detail view showing an exterior surface of the femoral portion of the lateral hinge of FIG. 15C.

FIG. 25A illustrates virtual positioning of the medial and lateral hinges relative to medial and lateral condyles on a model of external surfaces of a patient's limb;

FIG. 25B illustrates virtual positioning of tibial and femoral cuffs on the model of the external surfaces of the patient's limb; FIG. 25C illustrates the conception of the femoral cuff and hinge in a single piece, and the tibial cuff and tibial hinge as a single piece; and FIG. 25D illustrates a knee orthosis created from virtual models of the tibial and femoral pieces using additive manufacturing.

FIG. 26 is a schematic illustrating the production process of a bespoke knee orthosis.

DETAILED DESCRIPTION

In the following description, the same numerical references refer to similar elements. Furthermore, for the sake of simplicity and clarity, namely so as to not unduly burden the figures with several references numbers, not all figures contain references to all the components and features, and references to some components and features may be found in only one figure, and components and features of the present disclosure which are illustrated in other figures can be easily inferred therefrom. The embodiments, geometrical configurations, materials mentioned and/or dimensions shown in the figures are optional and are given for exemplification purposes only.

As will be explained below in relation to various embodiments, a knee orthosis with helicoidal axis is provided. Broadly described, the knee orthosis is designed to guide natural knee movement, based on most recent knowledge of knee anatomy and movement as will be described in more detail hereinafter. The knee orthosis can be tailored to conform to the specific anatomy of a wearer, for example based on the digitized surface of the wearer's inferior limb and fabricated using additive manufacturing techniques. Although the present disclosure focuses on embodiments of orthoses for the knee, it is appreciated that similar principles and configurations can apply to orthoses for other limbs.

Figure 1A:
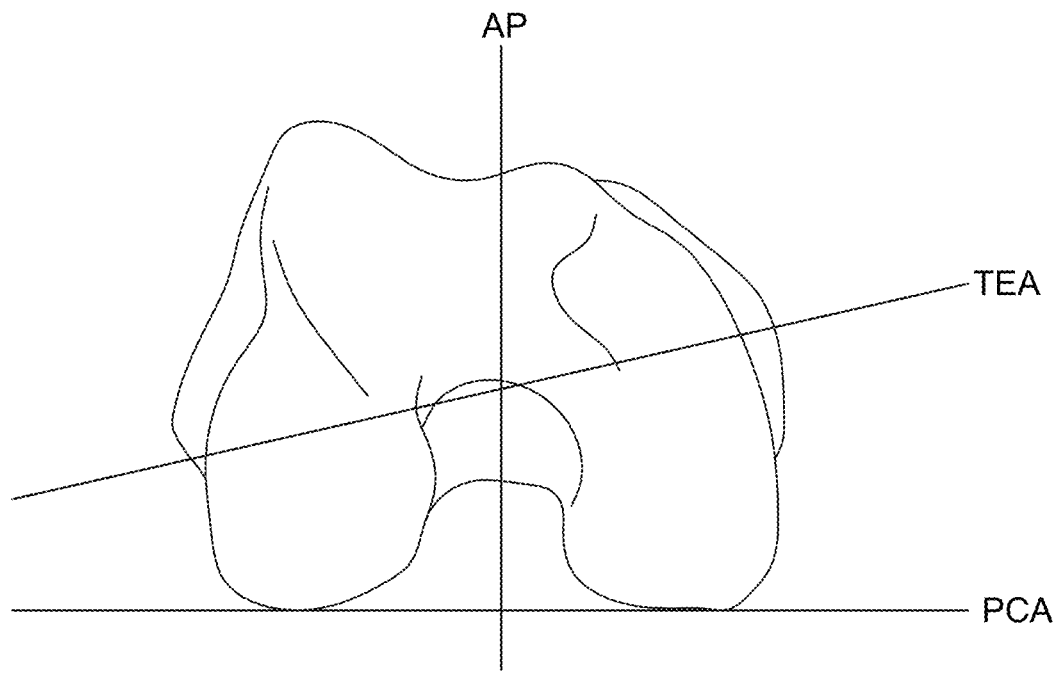
FIG. 1A is a distal end view of a femur showing the transepicondylar axis (TEA), the posterior condylar axis (PCA), and the anteriorposterior (AP) axis at the tibiofemoral joint.
Figure 1B:
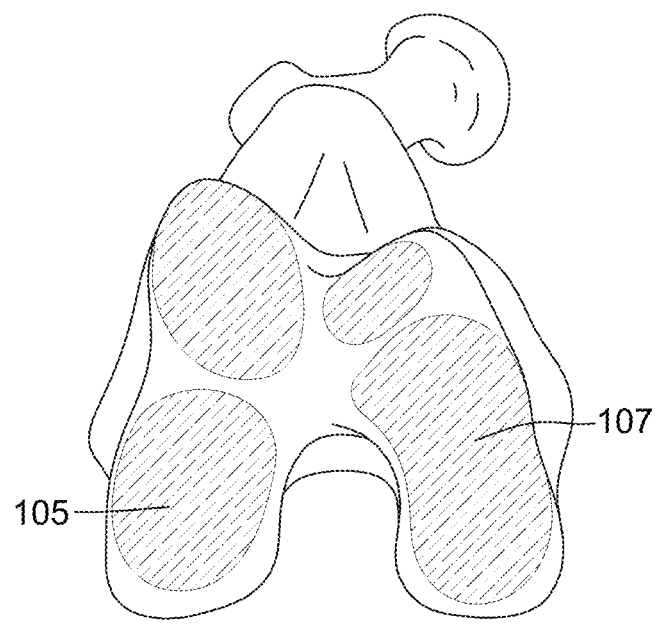
FIG. 1B is a distal end view of a femur showing the medial and lateral femoral condyles and the medial and lateral patellar surfaces.

With reference to FIGS. 1A and 1B, the alignment of the tibiofemoral joint, or knee, varies in reference to three planes, namely the frontal, sagittal and transverse planes. The tibiofemoral joint is a double condyloid joint with three degrees of freedom of angular (rotatory) motion and two degrees of sliding motion. Flexion and extension occur in the sagittal plane around a coronal axis through the epicondyles of the distal femur. Medial/lateral (internal/external) rotation occur in the transverse plane about a longitudinal axis through the lateral side of the medial tibial condyle. Abduction and adduction can occur in the frontal plane around an antero-posterior axis (AP), also referred to as Whiteside's Line.

Figure 2:
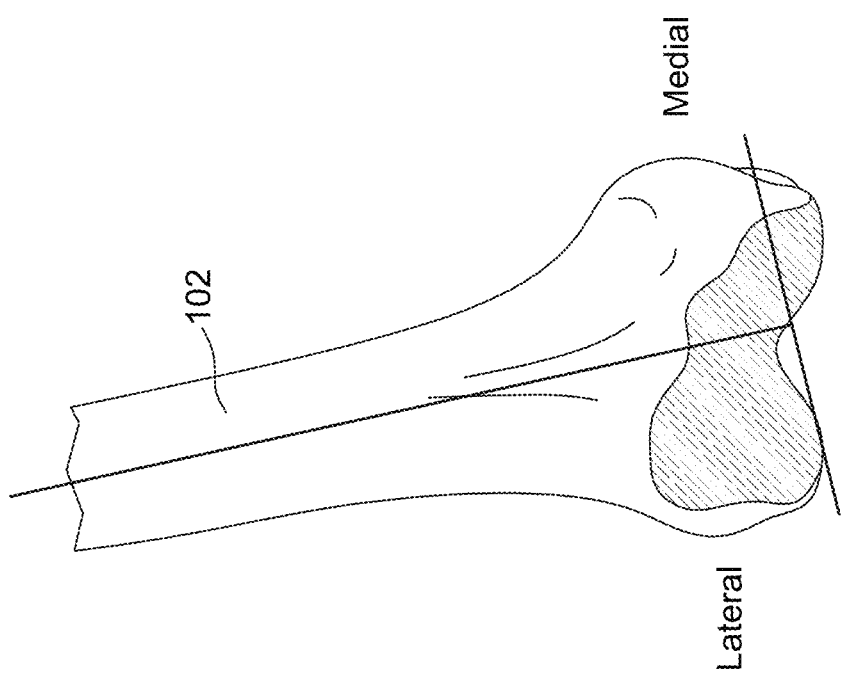
FIG. 2 is a side view a distal end of of a femur, showing the oblique position of the femoral shaft in relation to the femoral condyles.

With further reference to FIG. 2, the shaft of the femur has an oblique position. The lateral condyle 105 lies more directly in line with the shaft 102 and the medial condyle 107 extends further distally. The distal end of the femur remains essentially horizontal. In the sagittal plane, the condyles have a convex shape. In the frontal plane they present a slight convexity. The lateral femoral condyle 105 is shifted anteriorly in relation to the medial condyle 107, its articular surface is shorter and appears to be longer at its inferior section.

Figure 3A:
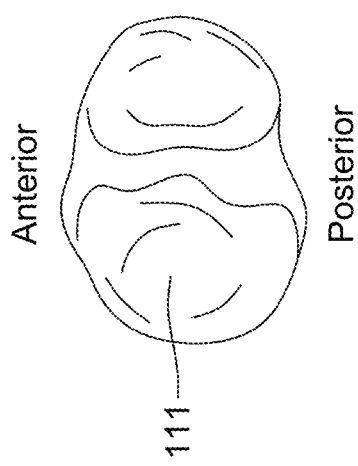
FIG. 3A is a proximal end view of a tibia, showing the tibial plateau and the asymmetrical attachments of the medial and lateral condyles thereon.
Figure 3B:
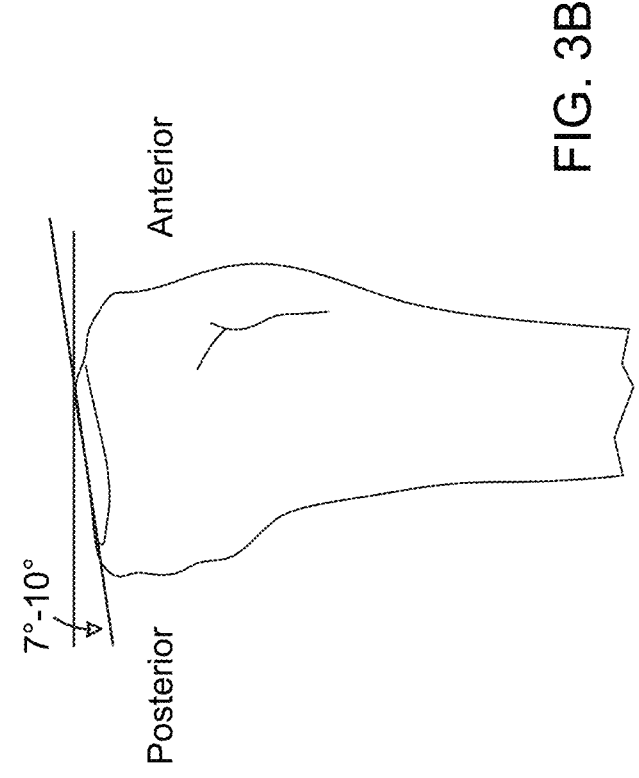
FIG. 3B is a side view of the proximal end of a tibia, showing posterior inclination of the tibial plateau.

As can be appreciated, the medial and lateral condyles 105 107 present asymmetrical attachments on the tibial plateau. As shown in FIG. 3A, the medial tibial plateau 111 is longer in the antero-posterior direction and the lateral tibial articular cartilage is thicker. As shown in FIG. 3B, the tibial plateau 111 is also inclined posteriorly approximately 7° to 10°. It is mainly flat, but there are convexities at the anterior and posterior margins.

Figure 4:
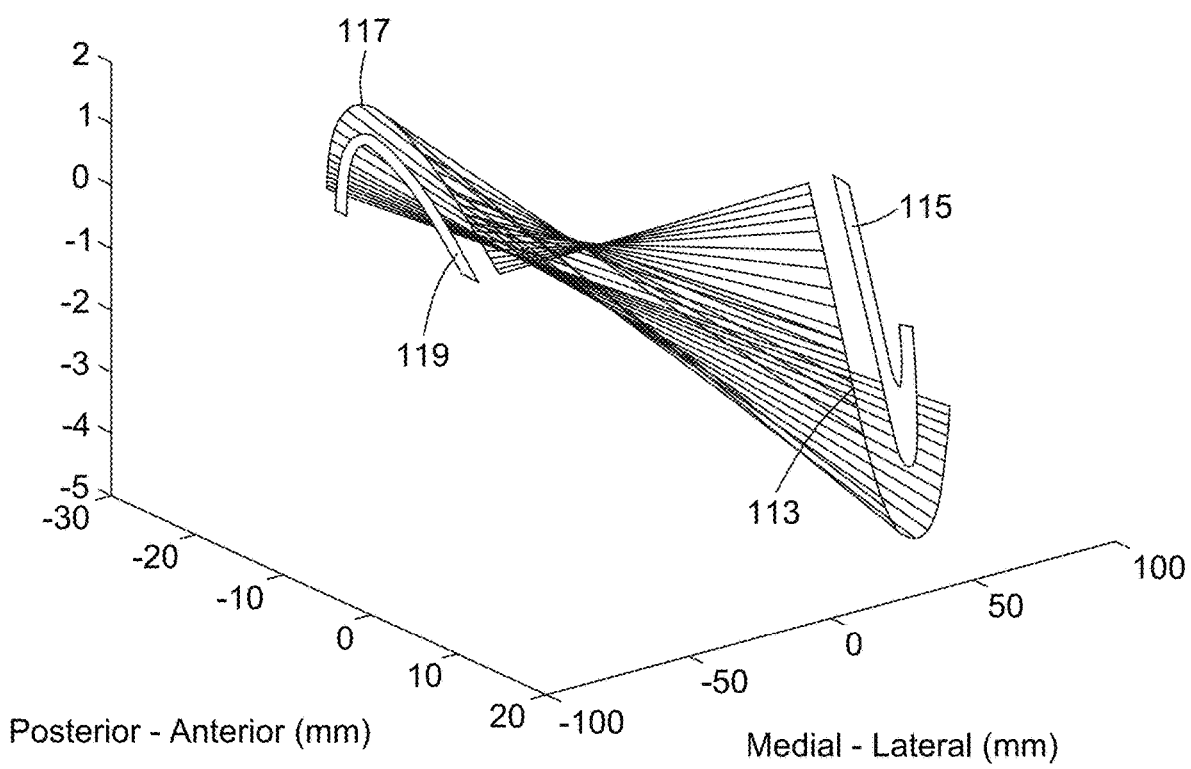
FIG. 4 is a 3D graph illustrating movement of the knee along an assymetrical helicoidal axis.

Due to the anatomy described above, the movement of the medial and lateral femoral condyles 105 107 causes the knee to follow a helicoidal axis of movement. As shown in FIG. 4, the axis of movement of the knee moves in space during flexion and extension in the knee. This axis of movement can be said to be helicoidal in that it comprises medial and lateral displacements about the center of the knee. In the illustrated embodiment, the axis is asymmetrically helicoidal in that the magnitude and/or path of the medial and lateral displacements are different. For example, during normal knee flexion, a medial extremity of the knee axis (i.e. corresponding to a medial anatomical joint 117) can displace a first distance posteriorly, whereas a lateral extremity of the knee axis (i.e. corresponding to a lateral anatomical joint 113) can displace a second distance anteriorly, with the first and second distances being different in magnitude. In the example illustrated in FIG. 4, the medial extremity of the knee axis translates posteriorly by approximately 2 to 4 mm corresponding to a posterior translation of the medial femoral condyle on the tibia. Similarly, the lateral extremity of the knee axis translates anteriorly by approximately 14-22 mm, corresponding to anterior translation of the lateral femoral condyle on the tibia. It is appreciated that similar translations of the medial and lateral condyles occur in reverse during extension of the knee.

Figure 5:
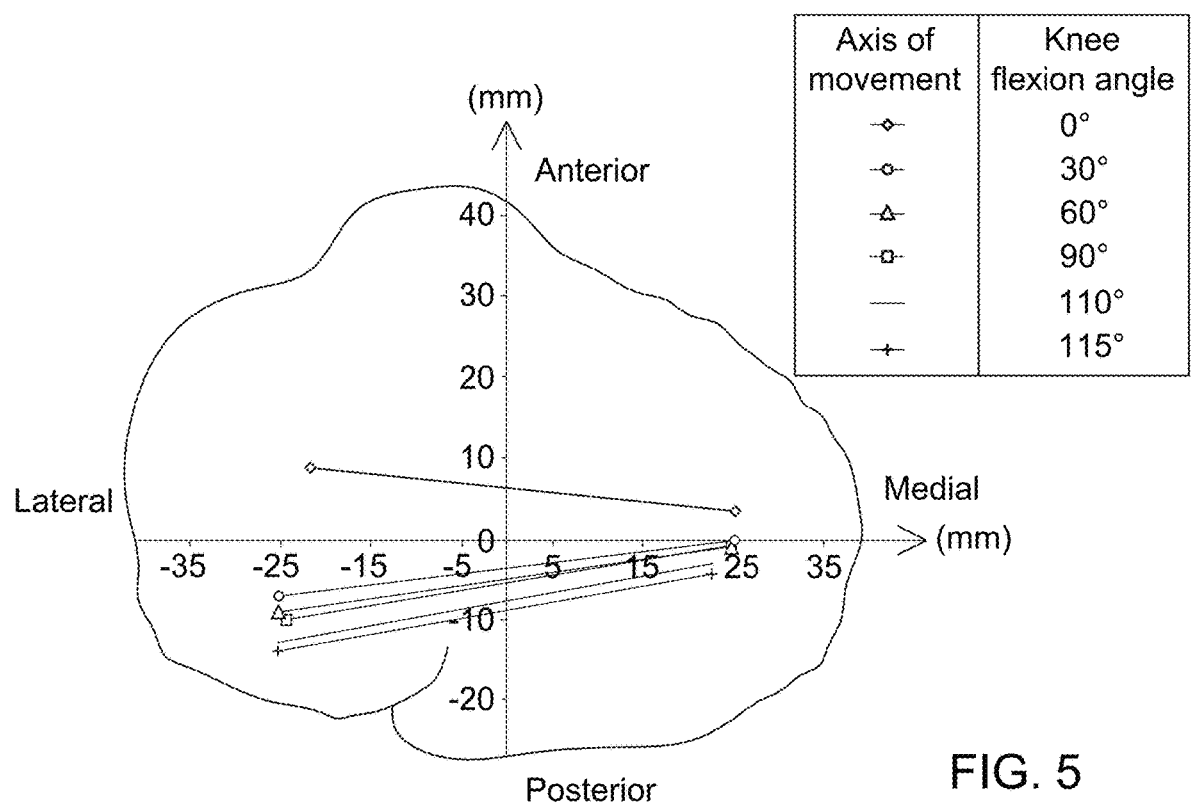
FIG. 5 is a 2D graph illustrating displacement of the helicoidal axis of the knee in reference to the tibial plateau.

It should be understood that in addition to the displacement of the extremities of the axis of movement, the center of the axis of movement also displaces during flexion and extension of the knee. As shown in FIG. 5, the axis of movement of the knee displaces posteriorly during flexion of the knee. As can be further appreciated, the magnitude of the axial rotation of the knee diminishes as the knee approaches both full extension and full flexion.

Figure 6:
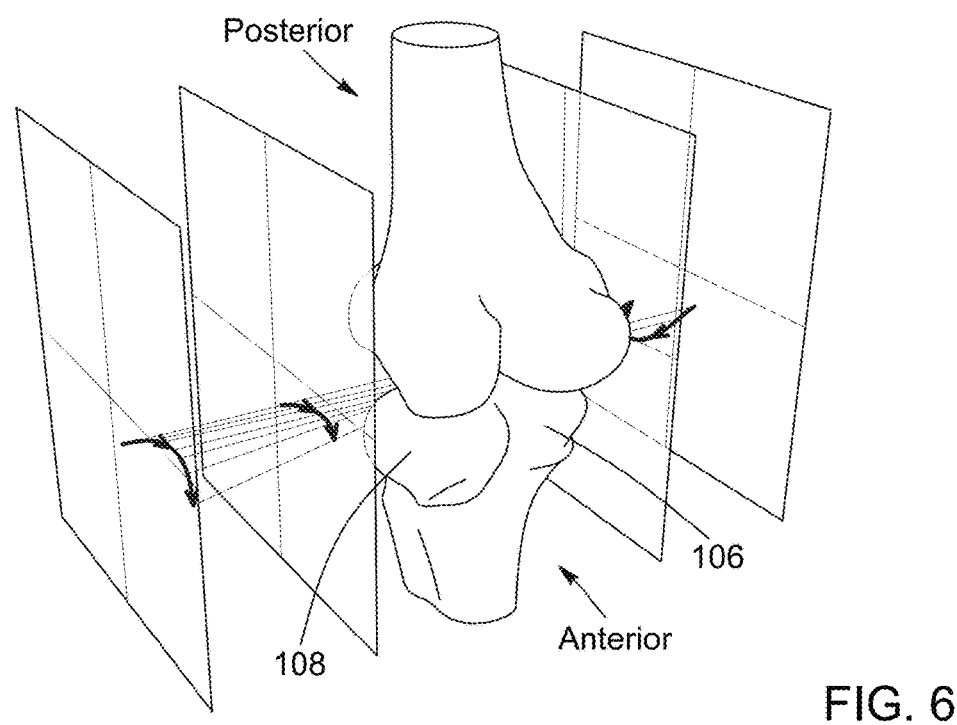
FIG. 6 is a perspective view of the tibiofemoral joint, showing movement of the medial and lateral condyles during axial rotation of the knee.
Figure 7:
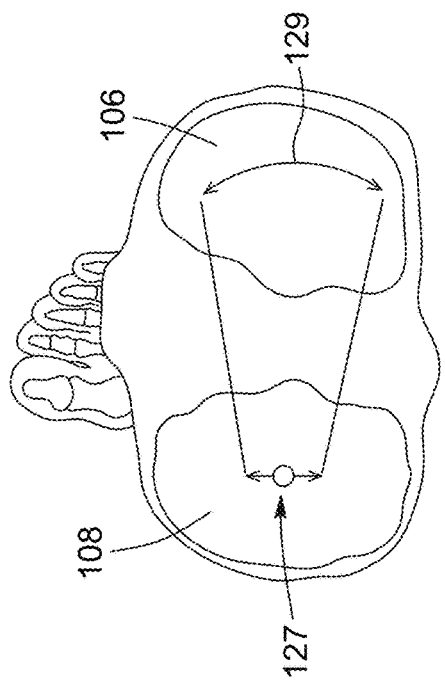
FIG. 7 is a schematic illustrating movement of the medial and lateral condyles on the tibial plateau.

As shown in FIG. 6, during tibial external rotation, the medial condyle 108 (i.e. medial anatomical joint) moves slightly anteriorly along a first arc, whereas the lateral condyle 106 (i.e. lateral anatomical joint) moves a larger distance posteriorly along a second arc. Similarly, during tibial internal rotation, the medial condyle 108 moves slightly posteriorly along its arc, whereas the lateral condyle 106 moves anteriorly a larger distance along its arc. As can be appreciated, the medial condyle 108 moves along a concave arc, i.e. an arc having an apex in a distal direction, whereas the lateral condyle 106 moves along a convex arc, i.e. an arc having an apex in the proximal direction. As can be further appreciated, as illustrated in FIG. 7, the medial condyle 108 acts as a pivot point 127 while the lateral condyle 106 moves through a greater arc of motion 129, regardless of direction of rotation.

Figure 8A:
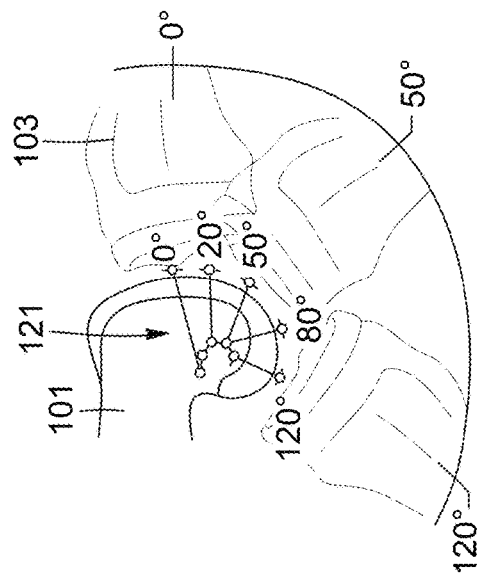
FIG. 8A is a side view of the tibiofemoral joint, showing posterior movement of the instant center of rotation during flexion of the knee.
Figure 8C:
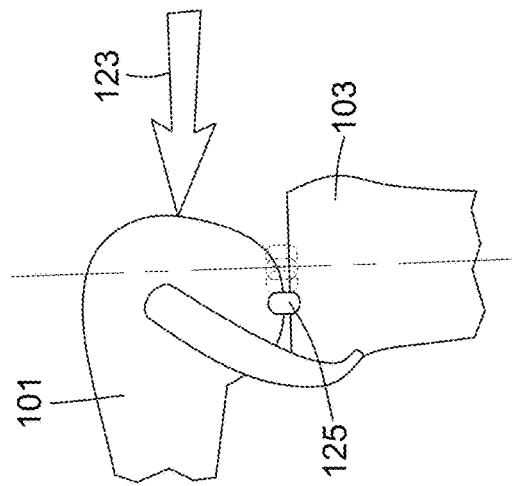
FIG. 8C is a schematic showing a posterior position of the tibiofemoral contact point during flexion of the knee.
Figure 8B:
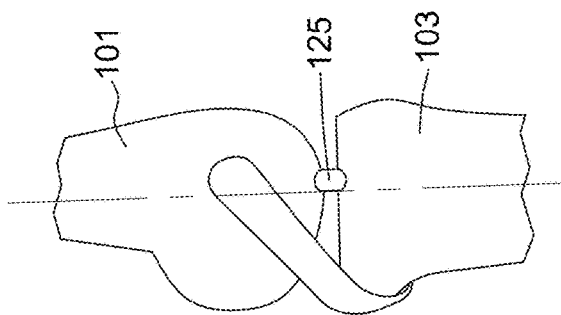
FIG. 8B is a schematic showing an anterior position of a tibiofemoral contact point during extension of the knee.

As shown in FIGS. 8A, 8B and 8C, the movement of the knee includes a posterior rollback component 123. As illustrated in FIG. 8A, the instant center of rotation 121 of the knee moves posteriorly as the knee is flexed. As illustrated in FIGS. 8B and 8C, when the knee is extended, a contact point 125 between the tibia 103 and femur 101 is positioned anteriorly, whereas when the knee is flexed, the contact point 125 moves towards a posterior position.

Figure 9:
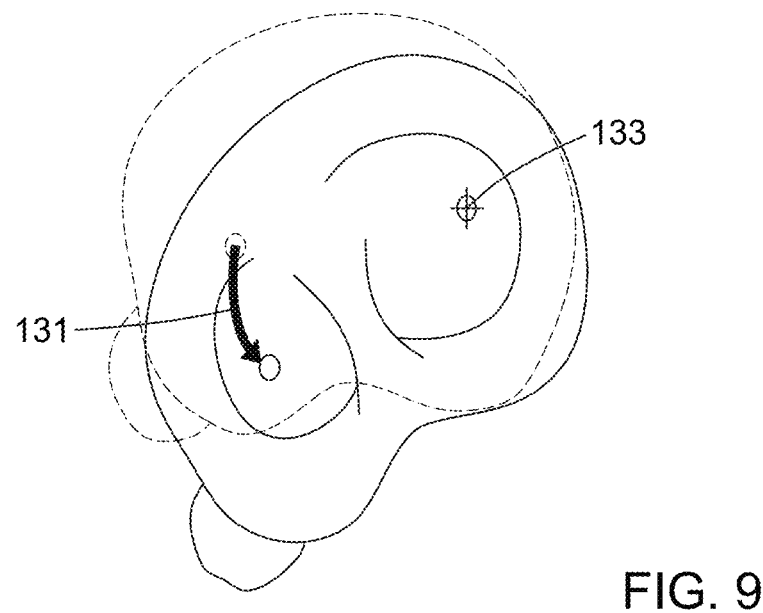
FIG. 9 is proximal end view of the tibia showing the mobile lateral compartment and the medial pivot in the concave tibial plateau.

The movement of the knee further includes a screw-home mechanism. As illustrated in FIG. 9, throughout external rotation of the tibia during knee extension and internal rotation of the tibia during knee flexion, the lateral condyle pivots 131 around a pivot 133 in the medial condyle, defining this screw home mechanism. This allows the knee to lock and decreases the work performed by the quadriceps while standing.

Figure 10:
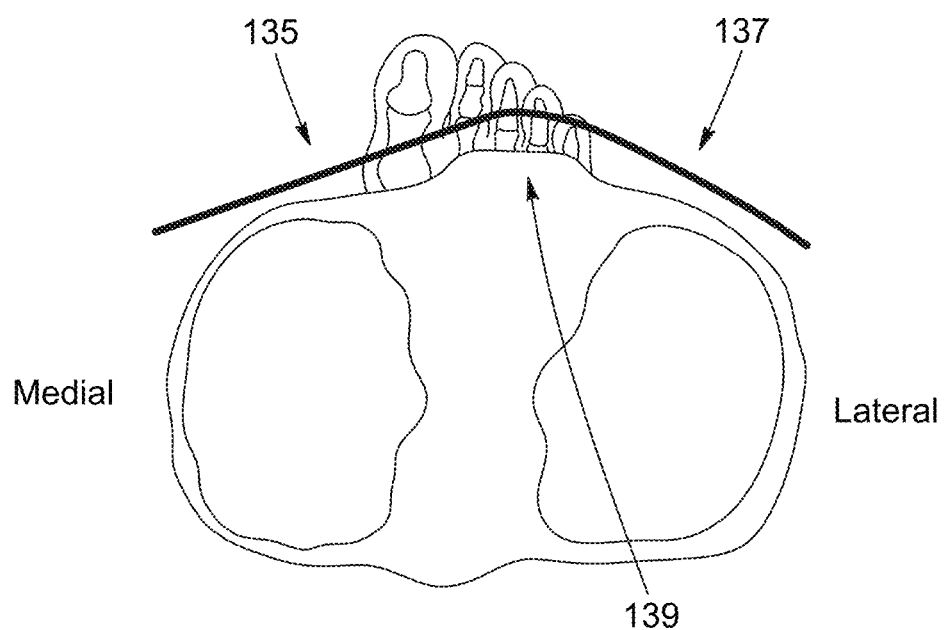
FIG. 10 is a schematic illustrating the flat medial surface and the curved lateral surface on either side of the tibial tubersosity.

As illustrated in FIG. 10, at the proximal and anterior section of the leg, the tibial tuberosity 139 forms the vertex of an angle with the medial and lateral surfaces of the tibia. The surface located on the medial side of the tibial tuberosity presents a flatter surface 135 in comparison to the lateral side 137. It can serve as a surface to stabilize the upper section of the tibial cuff of a knee orthosis and assist in controlling axial rotation of the leg.

Figure 11:
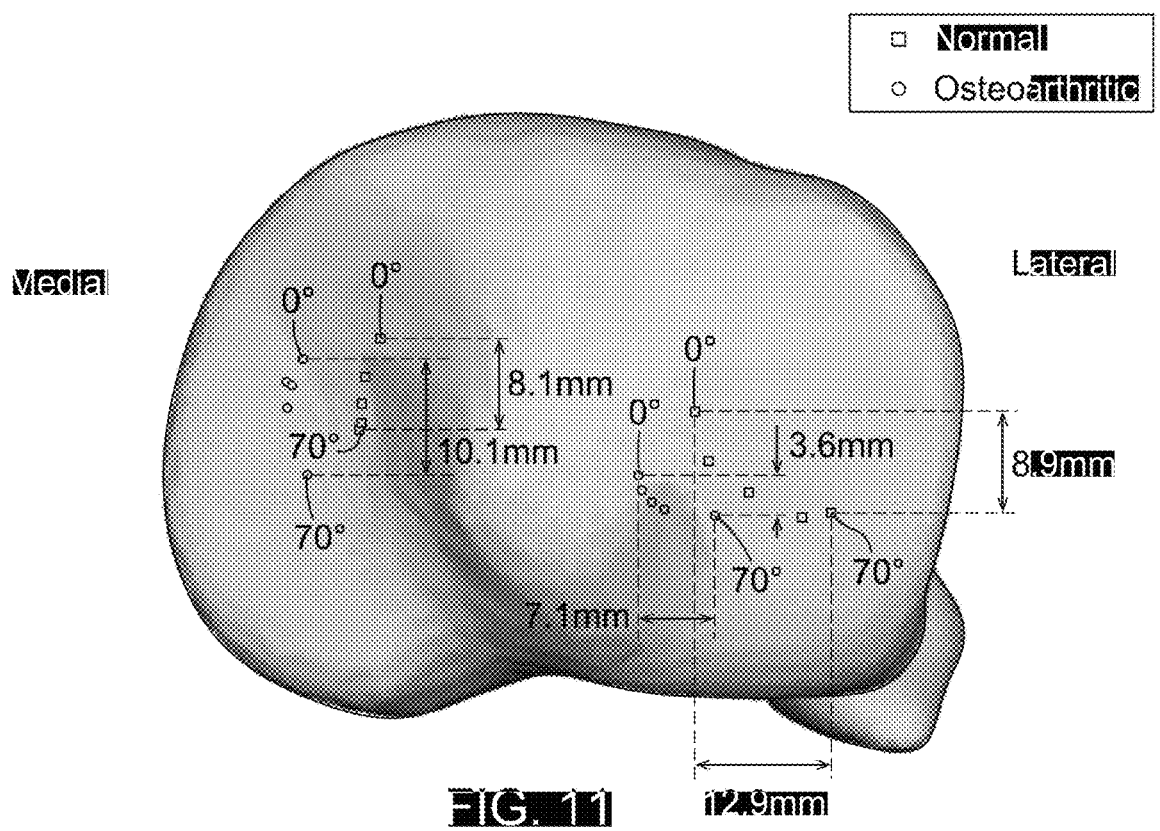
FIG. 11 is a schematic illustrating tibiofemoral contact points on the tibial plateau during squat in healthy and osteoarthritic subjects.

As can be appreciated, loading on the tibial plateau can vary between populations if knee structures are affected. For example, as illustrated in FIG. 11, the tibiofemoral contact points during squat movement can be displaced medially in osteoarthritic subjects, compared to healthy subjects. Correction of alignment of the tibiofemoral joint may therefore be necessary to move the contact points to correspond to those of a healthy subject.

Figure 12:
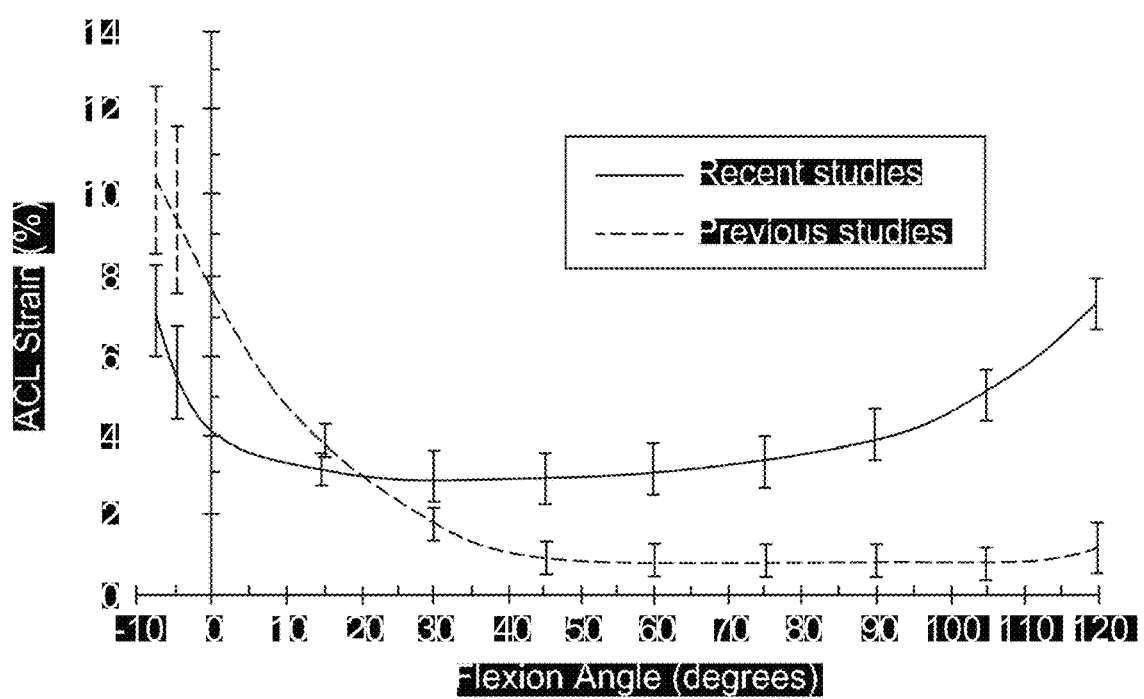
FIG. 12 is a graph illustrating variation of ACL strain according to knee flexion angle.
Figure 13A:
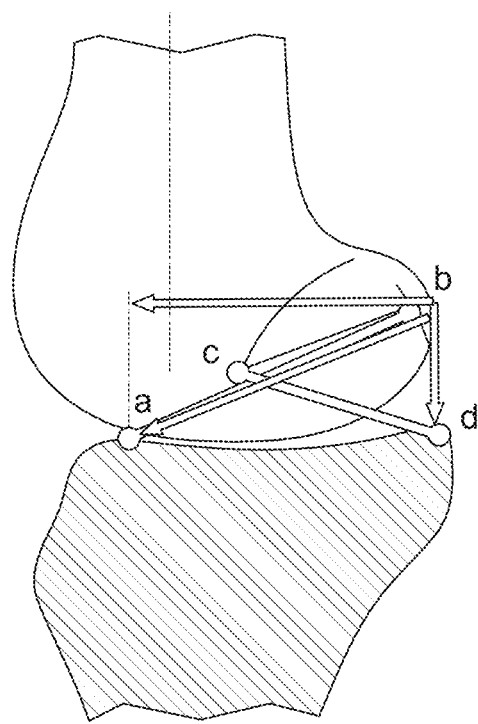
FIG. 13A is a schematic illustrating angle of ACL inclination during knee extension.
Figure 13B:
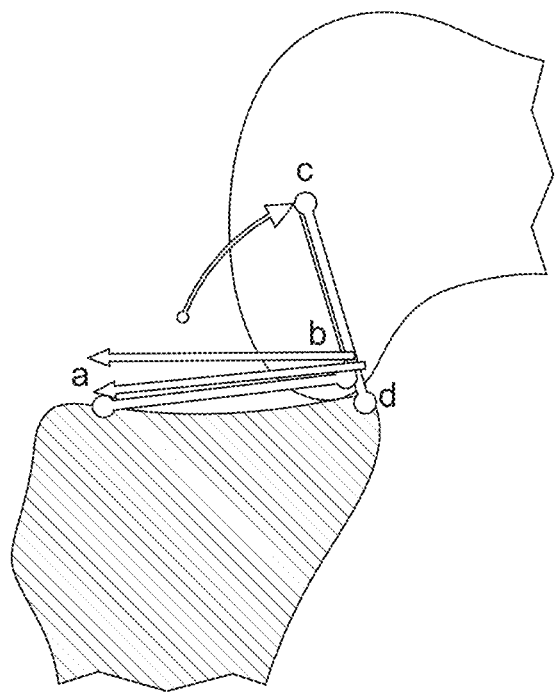
FIG. 13B is a schematic illustrating angle of ACL inclination during knee flexion.

Strain exerted at the anterior cruciate ligament (ACL) varies according to knee flexion angle. As illustrated in FIG. 12, strains on the ACL are greater when knee is fully flexed or extended. However, some portion of the ACL remains tight throughout the range of motion. As shown in FIG. 13A, at full knee extension, the angle of ACL inclination is the greatest and the anterior directed component force will eventually restrain posterior femoral roll. As shown in FIG. 13B, as knee flexion increases, the angle of ACL inclination decreases and the anterior directed component force increases sufficiently to produce anterior femoral slide.

As can be appreciated, the knee movements described above can be used to design a knee orthosis which guides a wearer's knee in a manner such that it follows a natural knee movement. More specifically, the knee orthosis can be designed with a hinge mechanism configured to cause the knee orthosis to flex and extend along an asymmetrical helicoidal pivot axis mirroring the natural asymmetrical helicoidal axis of movement of a knee as described above. The hinge mechanism can be configured to control movement along six degrees of freedom individually, in the frontal, sagittal, and transverse planes. In some embodiments, the orthosis can guide motion through five degrees of freedom, namely the three degrees of freedom of angular (rotatory) motion and two degrees of sliding motion, accounting for roll back and screw home mechanisms, among the other movement mechanisms described above. The orthosis can also be configured to realign a wearer's thigh in relation to the shin throughout movement of the knee, for example to correct the alignment by repositioning the tibiofemoral contact points to correspond to those of a healthy knee, and/or to adjust the alignment, for example to discharge worn areas of the knee.

Figure 14:
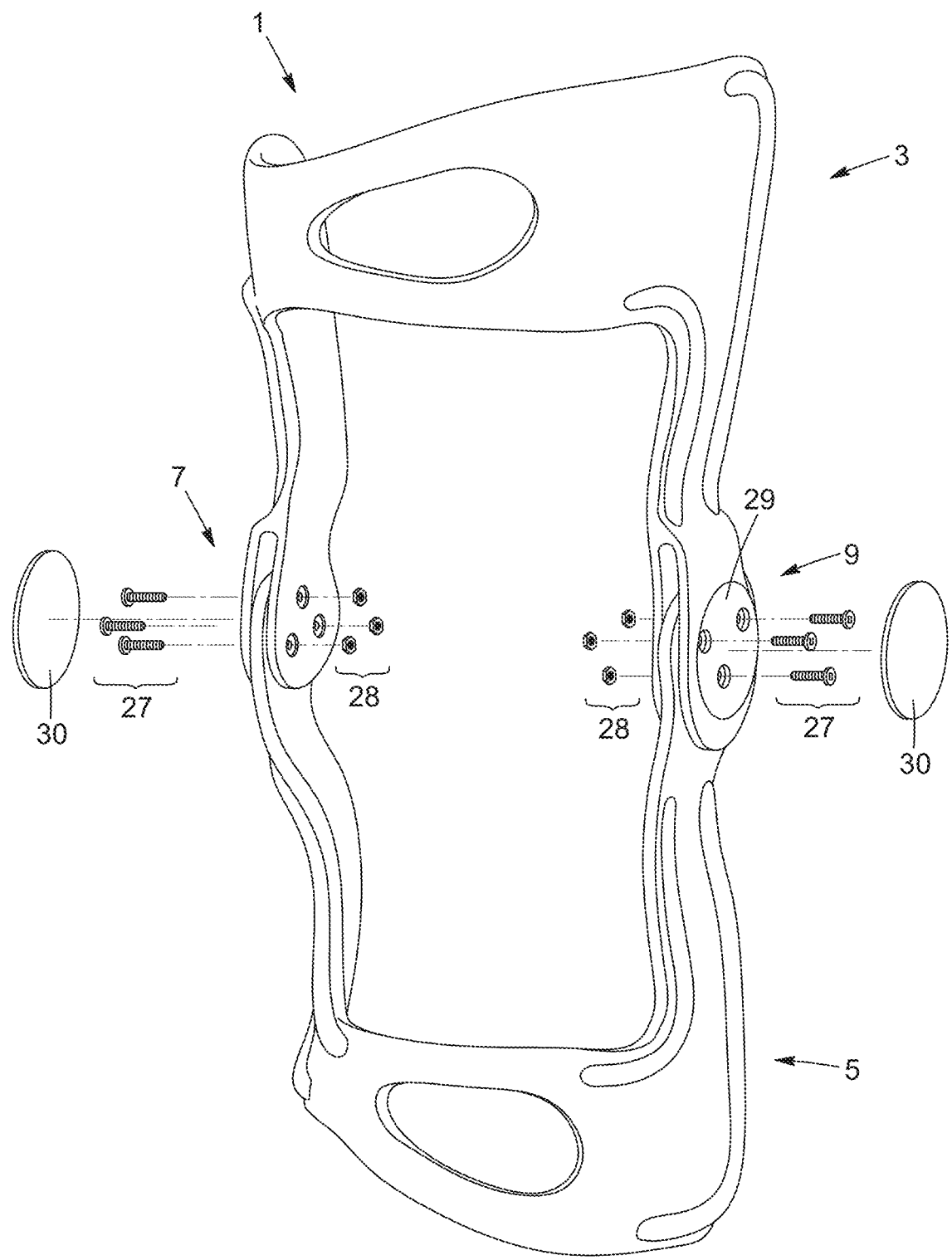
FIG. 14 is a perspective view of a knee orthosis configured to follow natural movement of a wearer's knee, according to an embodiment.
Figure 24:
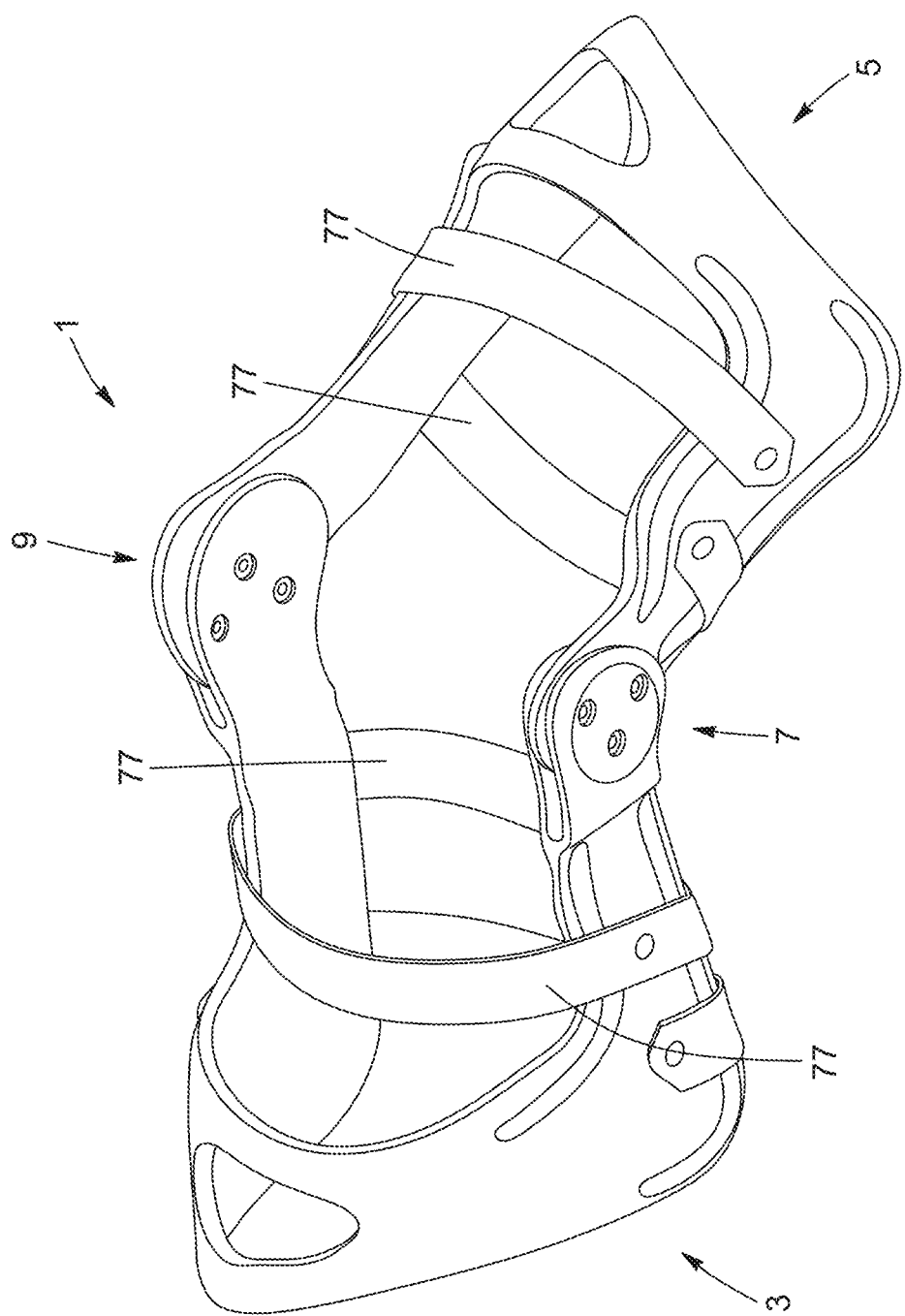
FIG. 24 is a perspective view of an assembled knee orthosis, according to an embodiment.
Figure 27B:
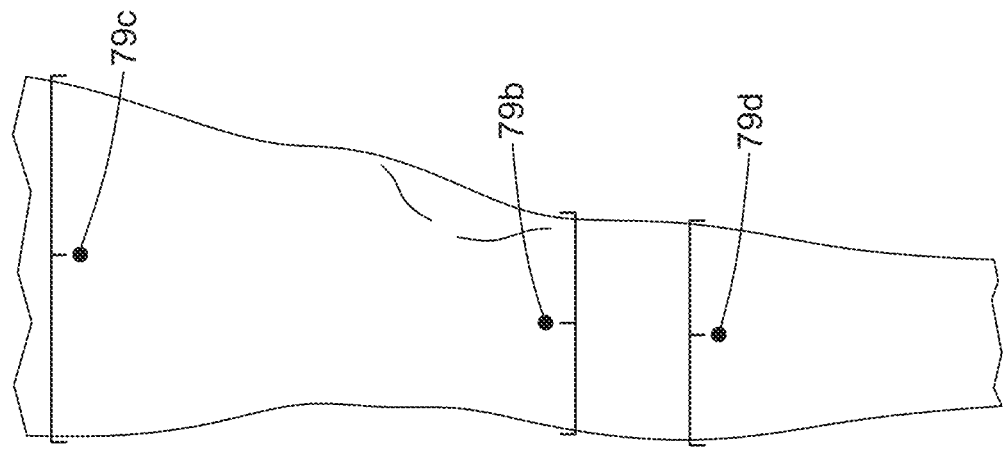
FIG. 27B is a lateral view of the wearer's leg showing a second group of landmarks.
Figure 27A:
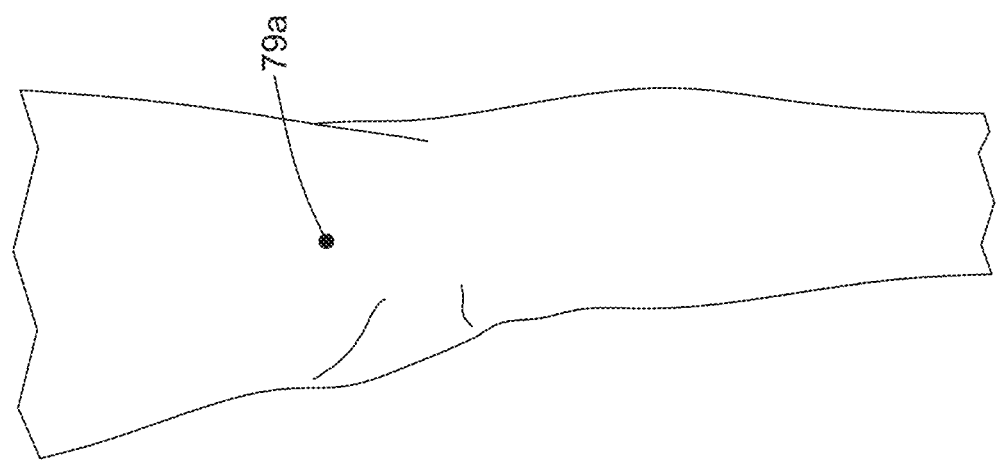
FIG. 27A is a medial view of a wearer's leg showing a first group of landmarks for virtual positioning of the knee orthosis components.
Figure 27D:
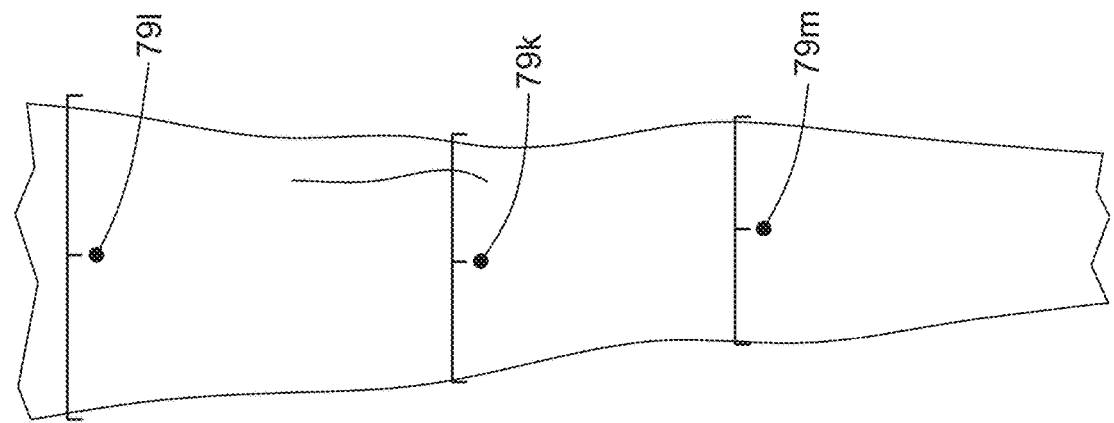
FIG. 27D is a posterior view of the wearer's leg showing a fourth group of landmarks.
Figure 27C:
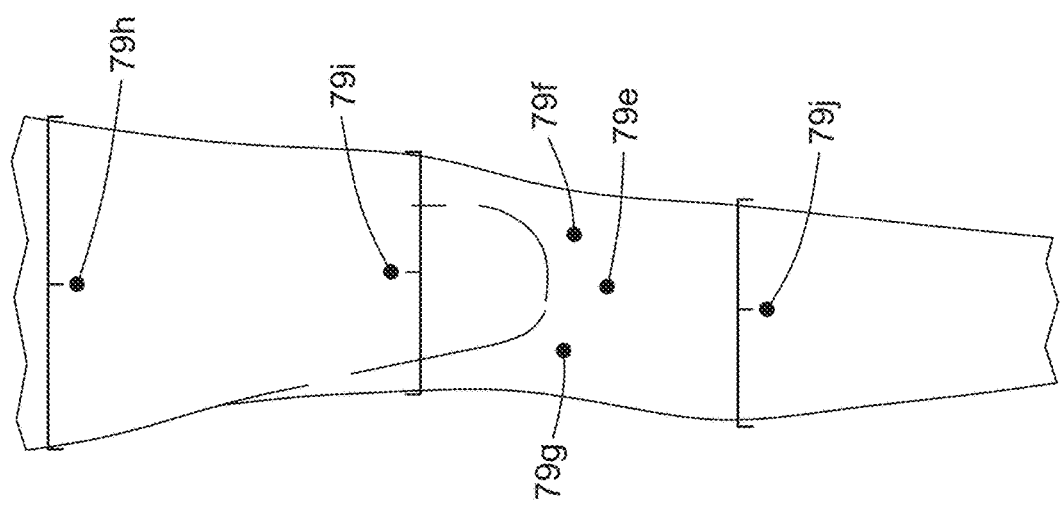
FIG. 27C is an anterior view of the wearer's leg showing a third group of landmarks.

With reference to FIG. 14, a knee orthosis 1 is shown according to an exemplary embodiment. The knee orthosis comprises a femoral section 3 for engaging relative to a wearer's femur, and a tibial section 5 for engaging relative to the wearer's tibia. The femoral 3 and tibial 5 sections are pivotally engaged with one another, defining an orthosis articulation which allows the orthosis 1 to move between an extended configuration in which an axis of the femoral 3 and tibial 5 sections are substantially aligned with one another (as shown in FIG. 14), and a flexed configuration in the axes of the femoral 3 and tibial 5 sections are angled relative to one another (as shown in FIG. 24). As can be appreciated, the orthosis 1 is configured to guide movement of the wearer's knee, and a full articulation of the orthosis 1 can correspond to a complete natural range of motion through flexion and extension of the wearer's knee, for example between 0° and 135°, although it is also possible that the full articulation of the orthosis 1 can correspond to a more limited range of motion according to the wearer's needs. For example, the full articulation can correspond to a range of extension/flexion between 10° and 120°, thus limiting full extension of the knee by 10° and preventing hyperextension thereof.

In the present embodiment, the femoral 3 and tibial 5 sections are pivotally engaged via a medial hinge 7 positioned medially relative to the wearer's knee, and a lateral hinge 9 positioned laterally relative to the wearer's knee. As will be described in more detail hereinafter, each of the medial 7 and lateral 9 hinges comprise superposed shells (i.e. members with substantially smooth surfaces bearing on one another) which are engaged with one another via fasteners 27 and configured to pivot relative to one another according to a predetermined path. Although in the present embodiment a medial 7 and lateral 9 hinge are provided, it is appreciated that in some embodiments, a single hinge can be provided on either the medial or lateral side depending on the needs of the wearer. As can be appreciated, a cap member 30 can be provided to hide fasteners 27 and can engaged in a corresponding recess 29 provided in medial 7 and/or lateral 9 hinges.

Figure 14A:
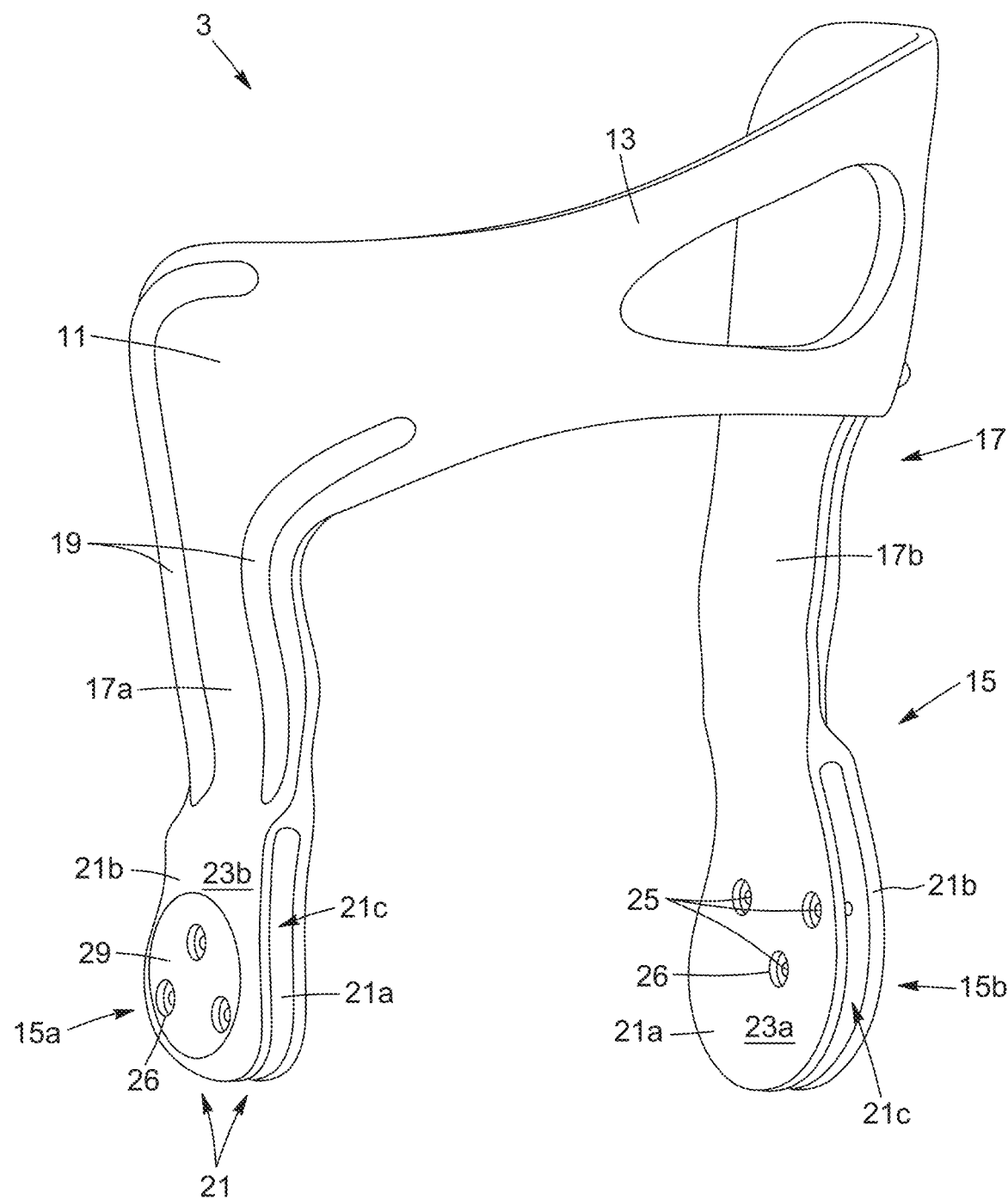
FIG. 14A is an individual view of a femoral section of the knee orthosis of FIG. 14.

In more detail now, and with reference to FIG. 14A, the femoral section 3 is shown in isolation. The femoral section 3 has a body 11 comprising a cuff 13 for engaging relative to the wearer's femur. In the present embodiment, the cuff 13 is a substantially rigid, curved member sized and shaped to follow a contour of an anterior surface of a wearer's thigh. The cuff 13 is configured to partially encircle the wearer's thigh and extends along the anterior side thereof, between the medial and lateral sides. It is appreciated that in other embodiments, the cuff 13 can fully or partially encircle the wearer's thigh and/or can be configured with rigid or flexible sections, or a combination thereof, depending on the needs of the wearer. Although the term "cuff" is used herein, it is appreciated that this member can correspond to any shape configured to engage relative to the wearer's femur.

The body 11 of the femoral section 3 further comprises a hinge 15 for forming a part of the articulation in the knee orthosis 1. In the present embodiment, the femoral hinge 15 comprises a medial component 15a for forming part of the medial hinge 7, and a lateral component 15b for forming part of the lateral hinge 9. Each of the medial 15a and lateral 15b components of femoral hinge 15 comprise a pair of spaced apart shells 21, namely an inner shell 21a positioned adjacent the wearer's leg, and an outer shell 21b spaced away from the inner shell 21a. In the present embodiment, inner 21a and outer 21b shells are positioned substantially parallel to one another and have defined therebetween a space or a slot 21c. In the present embodiment, as will be described in more detail hereinafter, the inner 21a and outer 21b shells have shapes corresponding to a segment of a sphere. Both shells 21a, 21b have the same spherical diameter, and are positioned such that their spherical segments run substantially parallel to one another.

In the present embodiment, the hinge 15 is spaced distally relative to the cuff 13 and is secured relative thereto via a rigid support member 17. More specifically, a medial end of the cuff 13 is secured relative to the medial component of the femoral hinge 15a via a medial component of support member 17a extending medially along the wearer's femur. Similarly, the lateral end of the cuff 13 is secured relative to the lateral component of the femoral hinge 15b via a lateral component of support member 17b extending laterally along the wearer's femur. As can be appreciated, support members components 17a, 17b can be shaped and configured to conform to a contour of the medial and lateral surfaces of the wearer's thigh. As can be further appreciated, support member components 17a, 17b can be configured with varying rigidity depending on the wearer's requirements. For example, rigidity structures 19 can be provided to increase or decrease stiffness/rigidity in desired sections of support member 17 and/or cuff 13. In the present embodiment, rigidity structures 19 comprise reinforcements, such as raised structures having extra material molded as part of the femoral section body 11, and openings formed in the cuff 13. It is appreciated, however, that other shapes and structures are possible to provide increased or decreased rigidity. For example, rigidity structures 19 can comprise lattices and/or voids. In some embodiments, rigidity structures 19 can comprise additional members or supports attached to body 11.

In the present embodiment, the body 11 of femoral section 3 is a unitary body in that it is formed as a single piece. In other words, the cuff 13, hinge 15 and support member 17 are all integrally formed as part of the same piece, without joints, fasteners, welds, adhesives, etc. securing these components together. As will be described in more detail hereinafter, this unitary body 11 can be formed using additive manufacturing techniques, such as 3D printing. The body 11 can be formed using different materials, such as plastic or metal and/or a combination thereof. Similarly, the body can be formed with different internal structures depending on rigidity and/or weight requirements.

Figure 14B:
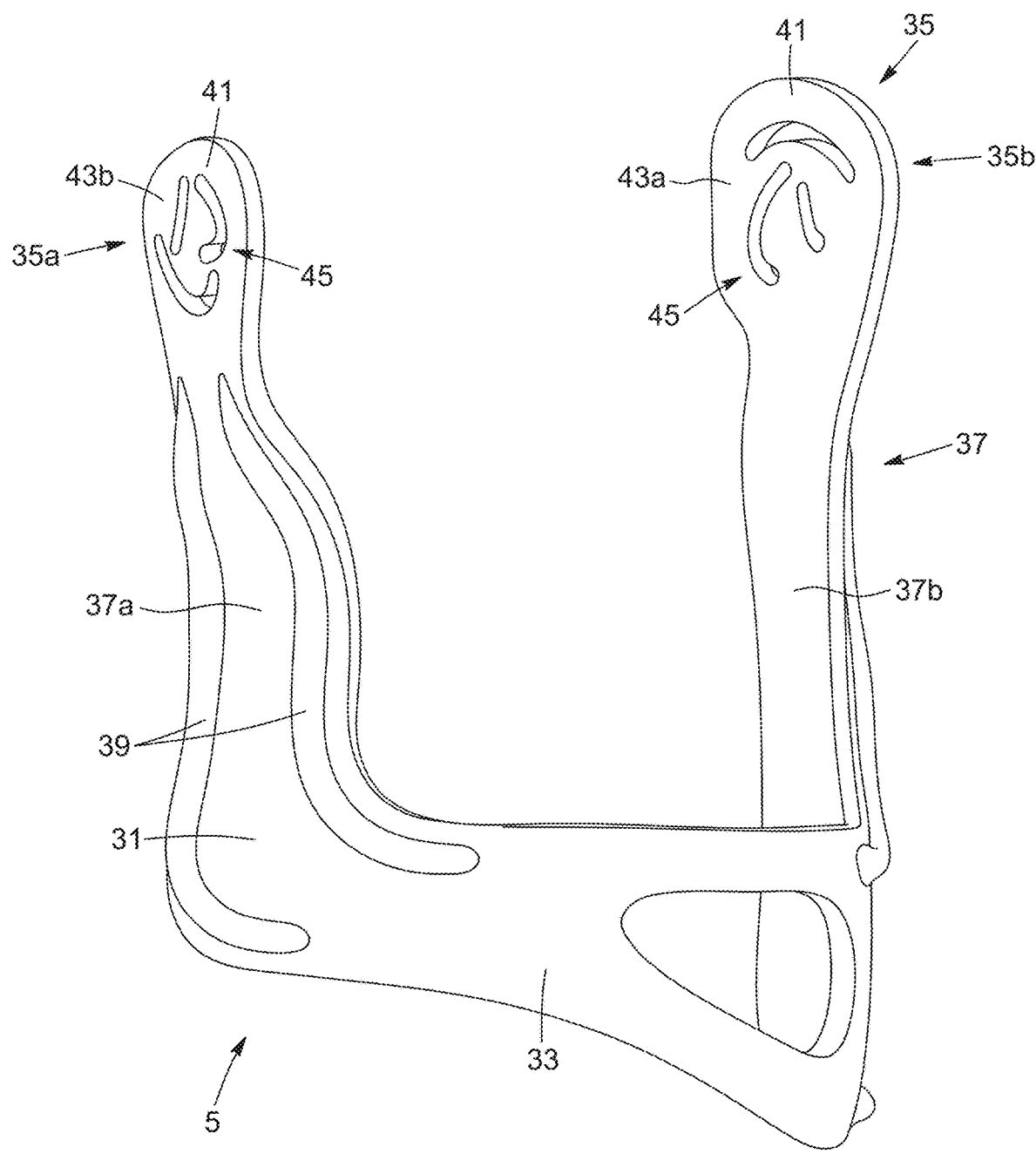
FIG. 14B is an individual view of a tibial section of the knee orthosis of FIG. 14.
Figure 16B:
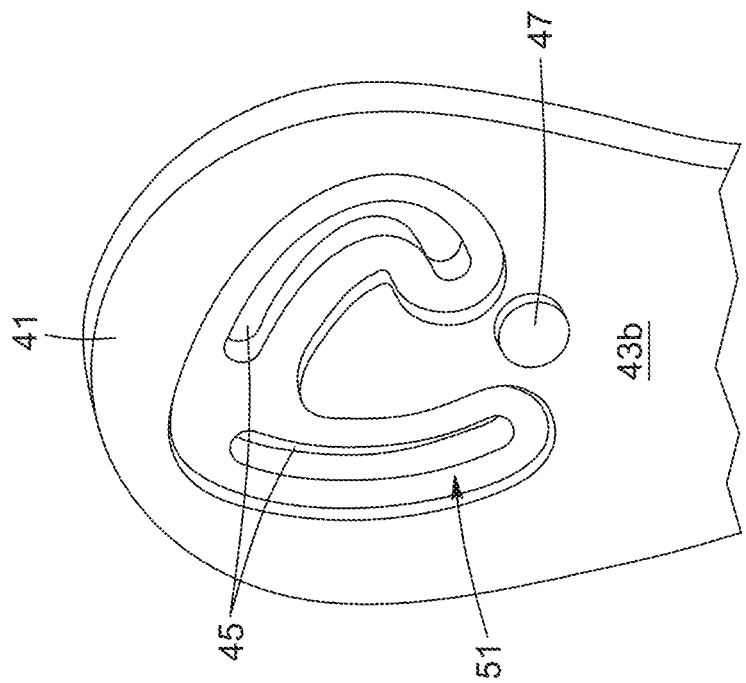
FIG. 16B is a detail view showing an exterior surface of the tibial portion of the lateral hinge of FIG. 16A.
Figure 16A:
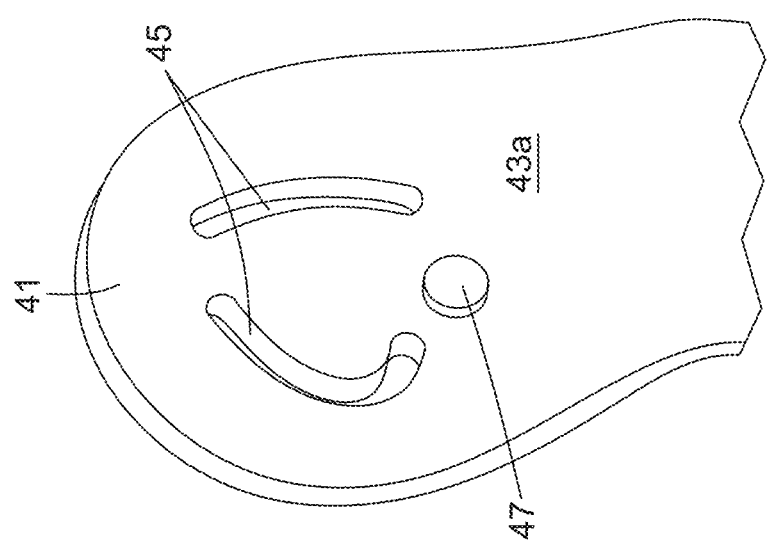
FIG. 16A is a detail view of a tibial portion of a lateral hinge, according to an alternate embodiment, showing an interior surface thereof.
Figure 16D:
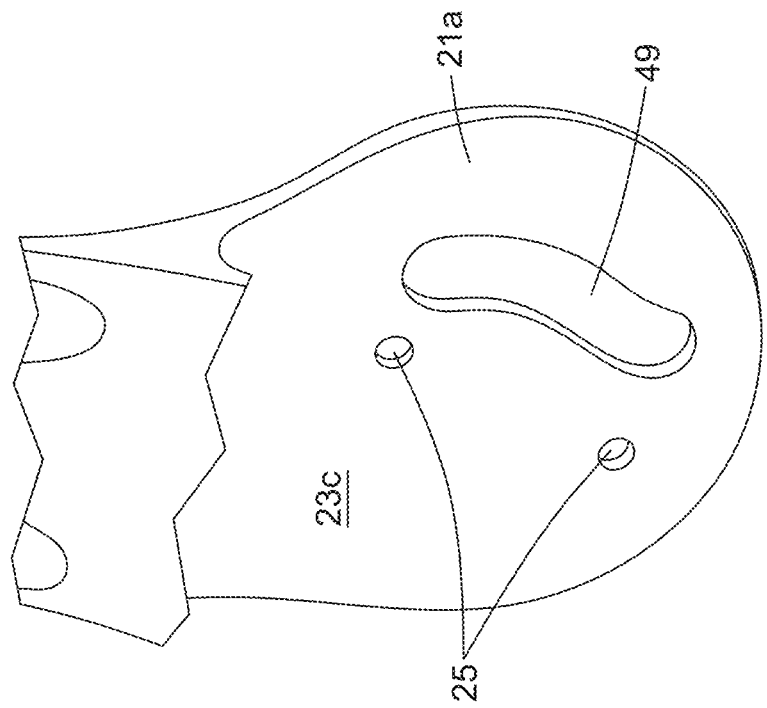
FIG. 16D is a detail view showing an exterior surface of the femoral portion of the lateral hinge of FIG. 16C.
Figure 16C:
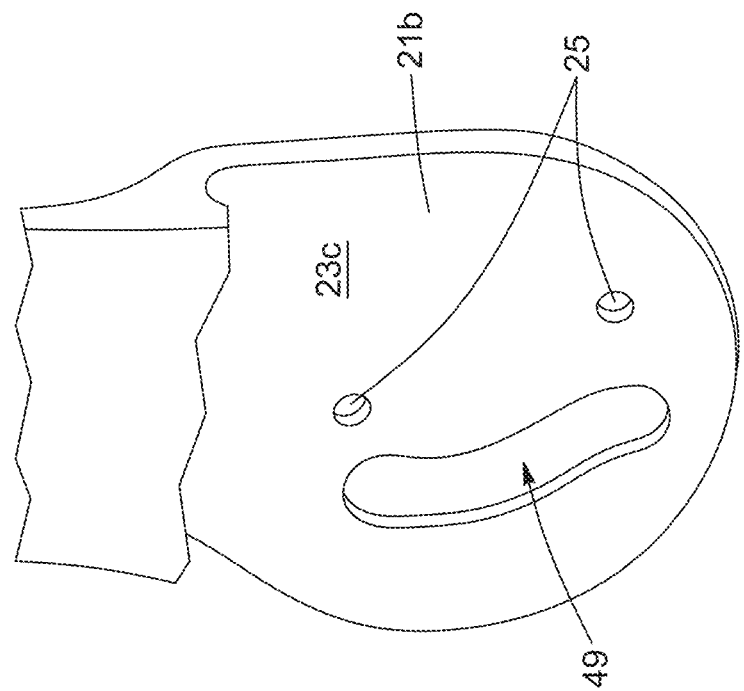
FIG. 16C is a detail view showing an interior surface of a femoral portion of the lateral hinge, according to an alternate embodiment.

With reference now to FIG. 14B, the tibial section 5 is shown in isolation. The tibial section 5 has a body 31 comprising a cuff 33 for engaging relative to the wearer's tibia. In the present embodiment, the cuff 33 is a substantially rigid, curved member sized and shaped to follow a contour of an anterior surface of a wearer's shin. The cuff 33 is configured to partially encircle the wearer's shin and extends along the anterior side thereof, between the medial and lateral sides. It is appreciated that in other embodiments, the cuff 33 can fully or partially encircle the wearer's shin and/or can be configured with rigid or flexible sections, or a combination thereof, depending on the needs of the wearer. Although the term "cuff" is used herein, it is appreciated that this member can correspond to any shape configured to engage relative to the wearer's tibia.

The body 31 of the tibial section 5 further comprises a hinge 35 for forming a part of the articulation in the knee orthosis 1. In the present embodiment, the tibial hinge 35 comprises a medial component 35a for forming part of the medial hinge 7, and a lateral component 35b for forming part of the lateral hinge 9. Each of the medial 35a and lateral 35b components of tibial hinge 35 comprise a shell 41 sized and shaped to engaged in the corresponding spacing or slot 21c of the femoral hinge 15.

In the present embodiment, the hinge 35 is spaced proximally relative to the cuff 33 and is secured relative thereto via a rigid support member 37. More specifically, a medial end of the cuff 33 is secured relative to the medial component of the tibial hinge 35a via a medial component of support member 37a extending medially along the wearer's tibia. Similarly, the lateral end of the cuff 33 is secured relative to the lateral component of the tibial hinge 35b via a lateral component of support member 37b extending laterally along the wearer's femur. As can be appreciated, support members components 37a, 37b can be shaped and configured to conform to a contour of the medial and lateral surfaces of the wearer's thigh. As can be further appreciated, support member components 37a, 37b can be configured with varying rigidity depending on the wearer's requirements. For example, rigidity structures 39 can be provided to increase or decrease stiffness/rigidity in desired sections of support member 37 and/or cuff 33. In the present embodiment, rigidity structures 39 comprise reinforcements, such as raised structures having extra material molded as part of the tibial section body 31. It is appreciated, however, that other shapes and structures are possible to provide increased or decreased rigidity. For example, rigidity structures 39 can comprise lattices and/or voids. In some embodiments, rigidity structures 39 can comprise additional members or supports attached to body 31.

In the present embodiment, the body 31 of tibial section 5 is a unitary body in that it is formed as a single piece. In other words, the cuff 33, hinge 35 and support member 37 are all integrally formed as part of the same piece, without joints, fasteners, welds, adhesives, etc. securing these components together. As will be described in more detail hereinafter, this unitary body 31 can be formed using additive manufacturing techniques, such as 3D printing. The body 31 can be formed using different materials, such as plastic or metal and/or a combination thereof. Similarly, the body can be formed with different internal structures depending on rigidity and/or weight requirements.

As mentioned above, the femoral 3 and tibial 5 sections engage with one another via femoral 15 and tibial 35 hinges. The femoral 15 and tibial 35 hinges each comprise shells 21, 41 which are superposed and engaged with one another to form medial 7 and lateral 9 hinges defining an articulation of the orthosis 1. The shells 21, 41 can be configured to rotated relative to one another following a predetermined path, such that each of the medial 7 and lateral 9 hinges move about respective first and second pivots. In this fashion, the orthosis 1 can articulate following a pivot axis which mimics the axis of rotation of natural knee movement. As can be appreciated, while the medial 7 and lateral 9 hinges can be designed symmetrically, their shells 21, 41 can be configured with different shapes allowing different (i.e. asymmetrical) paths of the pivots on either side of the wearer's knee, ultimately allowing the articulation of the orthosis 1 to follow a pivot axis which can move through six degrees of freedom (i.e. through the frontal, sagittal, and transverse planes).

With reference to FIGS. 15A and 15B a detail view of a lateral component 35b of a tibial hinge 35 is shown according to an embodiment. It is appreciated that a similar configuration can be provided for the medial component 35a of tibial hinge 35. The tibial hinge 35b comprises a tibial shell 41 having a substantially flat body having an interior surface 43a opposite an exterior surface 43b. As will be described in more detail hereinafter, surfaces 43a, 43b are configured to interface with and bear against corresponding surfaces of femoral shells 21 and have a sliding relationship therewith. Accordingly, surfaces 43a, 43b are substantially smooth to reduce friction. It is appreciated, however, that other configurations of surfaces 43a, 43b are also possible to reduce or increase friction as needed, for example via surface textures or bearing elements. The tibial shell 41 has a shape corresponding to a segment of a sphere having a constant diameter, with the interior surface 43a being substantially concave, and the exterior surface 43b being substantially convex, although it is appreciated that other configurations are possible. Guiding elements are provided guiding movement of the tibial shell 41 relative to the femoral shell 21. In the present embodiment, the guiding elements comprise three guide channels 45, corresponding to apertures opening on the interior 43a and exterior 43b surfaces, and each having a corresponding width and extending along a predetermined length and path. As can be appreciated, the length of the guiding elements can be adjusted to limit movements in certain directions.

A detail view of a lateral component 15b of a femoral hinge 15 for engaging with the lateral component 35b of the tibial hinge described above is shown in FIGS. 15C and 15D. It is appreciated that a similar configuration can be provided for the medial component 15a of the femoral hinge 15. The femoral hinge 15b comprises a pair of spaced apart shells 21, including an inner shell 21a and an outer shell 21b. The shells 21a, 21b have substantially flat bodies, and each have an interface surface 23c facing one another. As can be appreciated, the interface surfaces 23c of each shell 21a, 21b is configured to interface with and bear against a corresponding interior 43a or exterior 43b surface of tibial shell 41, and have a sliding relationship therewith. Accordingly, the interface surface 23c of each shell 21a, 21b can be substantially smooth to reduce friction. It is appreciated, however, that other configurations of interface surface 23c are also possible to reduce or increase friction as needed, for example via surface textures or bearing elements. The femoral shells 21a, 21b have a shape corresponding to a segment of a sphere having a constant diameter. In the present embodiment, the interface surface 23c of inner shell 21a is substantially convex to complement the concave shape of interior surface 43a of tibial shell 43, and the interface surface 23c of outer shell 21b is substantially concave to complement the convex shape of exterior surface 43b of tibial shell. As can be appreciated, the femoral 21 and tibial 41 shells can all have the same spherical diameter, with their spherical curves being positioned parallel to one another. Guiding elements are provided for guiding movement of the femoral shells 21 relative to the tibial shell 41. In the present embodiment, the guiding elements comprise three apertures 25 in each of the shells 21a, 21b, opening on the interior 23a and hinge interface 23c surfaces of the inner shell 21a, and opening on the exterior 23b and hinge interface 23c surfaces of the outer shell 21b. As can be appreciated, apertures 25 are positioned in alignment with corresponding guide channels 45 of the tibial shell 41, and are sized and shaped to receive a corresponding fastener 27, such as a pin, therethrough. The pin/fastener 27 can thus be fixed relative to femoral shells 21, allowing tibial shell 41 to move relative thereto while being guided by channels 45. In the present embodiment, as shown in FIGS. 14 and 14A, pin/fastener 27 is secured via a corresponding nut 28. Moreover, a recess or set 26 is provided around apertures 25 to allow the fastener head 27 and/or nut 28 to remain flush with surfaces 23a, 23b. It is appreciated that other configurations are also possible.

Although particular configurations of femoral 21 and tibial 41 shells where shown above, it is appreciated that other configurations are possible. For example, an alternate embodiment of femoral 21 and tibial 41 shells are shown in FIGS. 16A-16D. In the illustrated embodiment, tibial shell 41 is provided with two guiding channels 45. Tibial shell 41 further includes a pin member 47 extending from both the interior 43a and exterior 43b surfaces. In the present embodiment, the pin member 47 is molded as part of the unitary body 31 of tibial section 5, and is a rounded protrusion formed on interior 43a and exterior 43b surfaces. Other configurations of pin member 37 are also possible. For example, pin member can be a separate element extending through an aperture in tibial shell 41. Femoral shells 21 is configured in a complimentary fashion to engage with tibial shell 41. More specifically, femoral shells 21a, 21b each comprise two apertures 25 for receiving fasteners/pins for engaging with corresponding guide channels 45 of the tibial shell 41. Femoral shells 21a, 21b further comprise flail guiding channels 49 for receiving pin member 47 and guiding the same along a predetermined path. In the present embodiment, guiding channels 49 are recessed grooves opening on the interface surface 23c of shells 21a, 21b, and having a depth for accommodating the pin member 47. It is appreciated, however, that other configurations are possible. For example, guiding channels 49 can be apertures opening on the interface surface 23c and on the interior 43a and exterior 43b surfaces.

As can be appreciated, different combinations of pin elements 27, 47, and guide channels 25, 45 are possible depending on the requirements of the orthosis 1. In the present embodiment, three guiding elements are provided for controlling movement of the hinges along six degrees of freedom, but it is appreciated that more guiding elements can be provided to limit certain movements of the orthosis 1 articulation. For example, in some embodiments, four or five guiding elements can be provided in the form of four or five channels in combination with four or five pins. It is further appreciated that the guiding elements can comprise different combinations of pins 27, 47 and channels 25, 45, positioned on the femoral 21 and/or tibial 41 shells as needed. For example, in some embodiments all guiding elements can comprise pins molded in tibial shell and flail corresponding channels in femoral shells, whereas in other embodiments, a different number of guiding elements can comprise molded pins. It is further appreciated that other types of guiding elements are also possible.

Figure 17B:
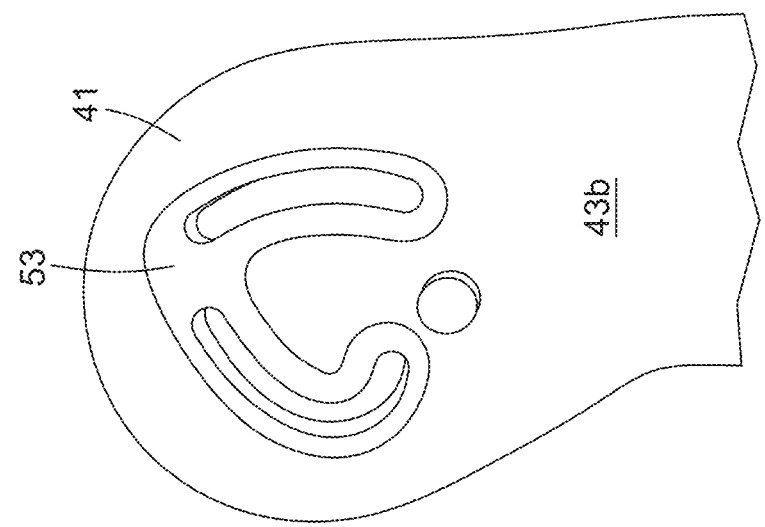
FIG. 17B is a detail view of the tibial portion of a lateral hinge of FIG. 17A, showing the reinforcement plate inserted in its corresponding recess such that it is flush with the exterior surface.
Figure 17A:
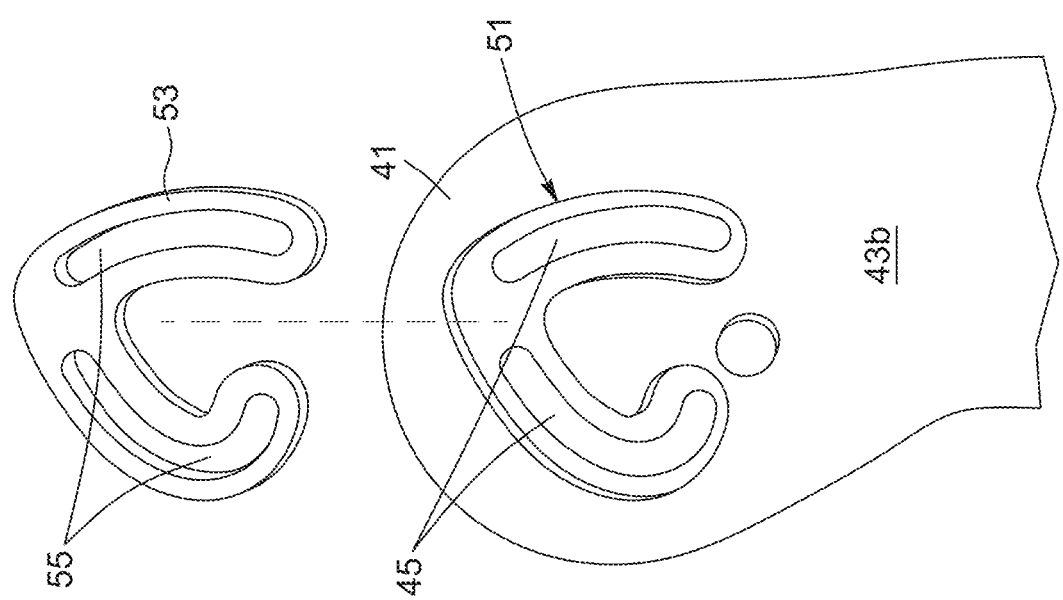
FIG. 17A is an exploded view of a tibial portion of a lateral hinge, according to an alternate embodiment comprising a reinforcement plate.

In some embodiments, the channels 25, 45 can be reinforced if needed. For example, as illustrated in FIGS. 17A and 17B, tibial shell 41 can comprise a recess 51 around guiding channels 45. A reinforcement plate 53 made out of a rigid material, such as metal, can be positioned in the recess 51, around guiding channels 45, such that it remains flush with surface 43b. In the present embodiment, the reinforcement plate 53 comprises apertures 55 corresponding to the size and shape of channels 45 and positioned in alignment therewith.

It is appreciated that the configuration of the shells can be designed to respect several constraints. For example, to respect esthetic constraints, the lateral and medial hinges can have different shapes, and the grooves in the tibial hinge can be configured to be maximally covered. Similarly, to respect functional constraints, the connection between the hinges and the cuff can respect the width of the cuff, there can be sufficient space between grooves in the tibial shell to ensure solidity of the tibial shell, and the size of the hinges can me minimized to avoid encumbrances.

Figure 18:
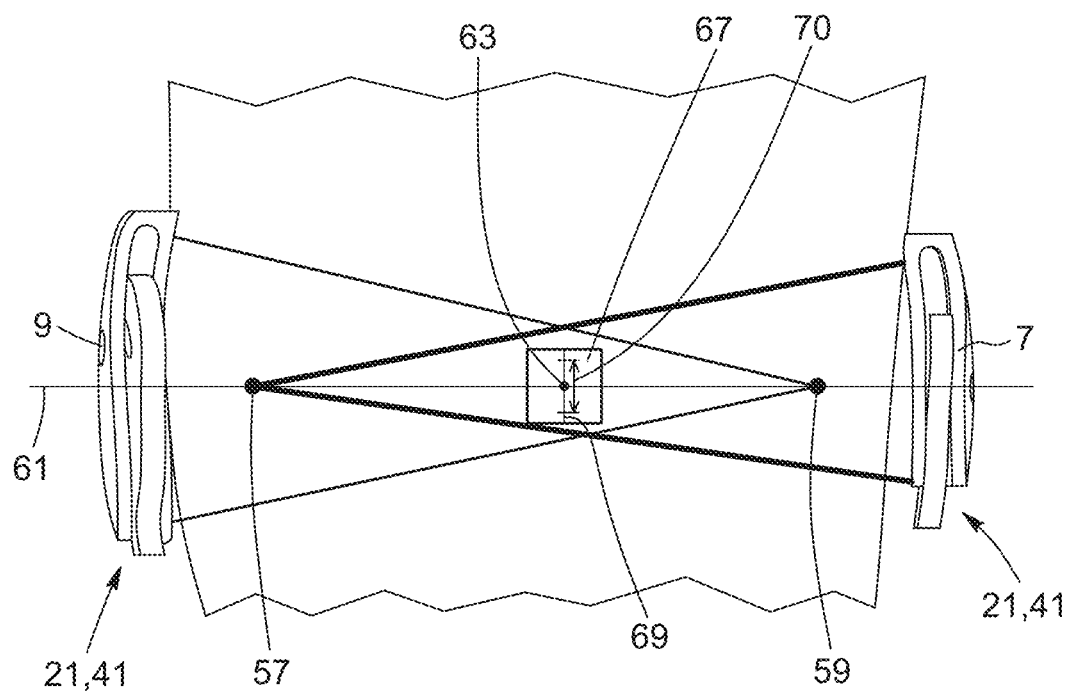
FIG. 18 is a schematic representation of the independent geometrical center of the medial and lateral shells which coincides with the helicoidal axis of movement of the knee.

As can be appreciated, the geometry of the medial 7 and lateral 9 hinges and their corresponding shells 21, 41, along with the configuration of guiding elements (including shape and position of guiding channels 25, 45) can be selected to constrain the knee orthosis 1 to articulate in a manner which closely matches natural knee movement of the wearer. An exemplary embodiment of hinge geometry is shown in FIG. 18. In the illustrated embodiment, the shells 21, 41 in the medial hinge 7 are shaped as an arc of a sphere having a first diameter, and the shells 21, 41 in the lateral hinge 9 are shaped as an arc of a sphere having a second diameter. The first and second diameters are different such that each of the hinges 7, 9 have different geometrical centers 57, 59. As can be further appreciated, the geometrical centers 57, 59 will displace in 3D space independently from one another. In the present embodiment, the hinges 7, 9 are configured such that the geometric center 57 of the medial hinge 7 and the geometric center 59 of the lateral hinge 9 do not coincide with one another throughout the full articulation of the orthosis 1. In other words, at no point during flexion and extension of the orthosis 1 do the geometric centers 57 and 59 overlap in 3D space. More specifically, in the present embodiment, throughout the full articulation of the orthosis 1, the geometric centers 57 and 59 further do not coincide with a common sagittal plane, but can intersect with a common transverse 65 and/or frontal 67 plane. For example, from a frontal view (i.e. as viewed in FIG. 18), it can appear as though centers 57 and 59 intersect at different points along a common line 61, but do not coincide at a single point along said line 61 throughout the full articulation of the orthosis 61.

Figure 19:
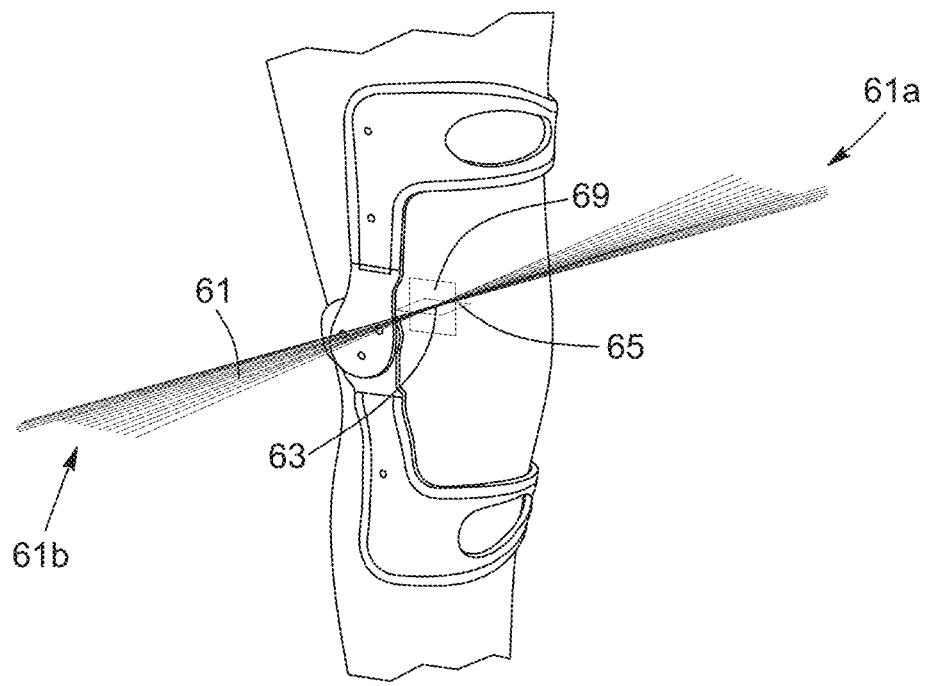
FIG. 19 is a schematic of an embodiment of an orthosis positioned on a wearers knee, showing the knee helicoidal axis of rotation.

As can be appreciated, the pivot axis of the orthosis articulation can correspond to the line 61 drawn between the geometric centers 57, 59n. In other words, the hinges 7, 9 are configured such that the geometric centers 57, 59 coincide with a common pivot axis 61. As can be appreciated, as the hinges 7, 9 are articulated between extended and flexed positions, the geometric centers 57, 59 will displace, causing the pivot axis 61 to move as well. However, the movement of hinges 7, 9 can be constrained via shells 21, 41 to move about their pivots, such that the movement of pivot axis 61 follows a predetermined path, for example throughout six degrees of freedom through transverse 65, frontal 67, and sagittal 69 planes. As shown in FIG. 19, the hinges 7, 9 can be configured such that the common pivot axis 61 corresponds to the asymmetric helicoidal axis of movement of the wearer's knee, with each extremity 61a, 61b of the pivot axis 61 following a different, independent arcuate path in 3D space, for example through six degrees of freedom. In this fashion, the pivot axis can be configured to follow an instantaneous axis of movement of the wearer's knee. As can be appreciated, a center 63 of the pivot axis 61 can be defined, for example at a midpoint between geometric centers 57, 59, and the hinges 7, 9 can be configured such that the center 63 is constrained to move within a predetermined range 70 in a sagittal plane 69, such that movements of the hinges 7, 9 guide a mediolateral displacement of the wearer's knee.

Figure 22:
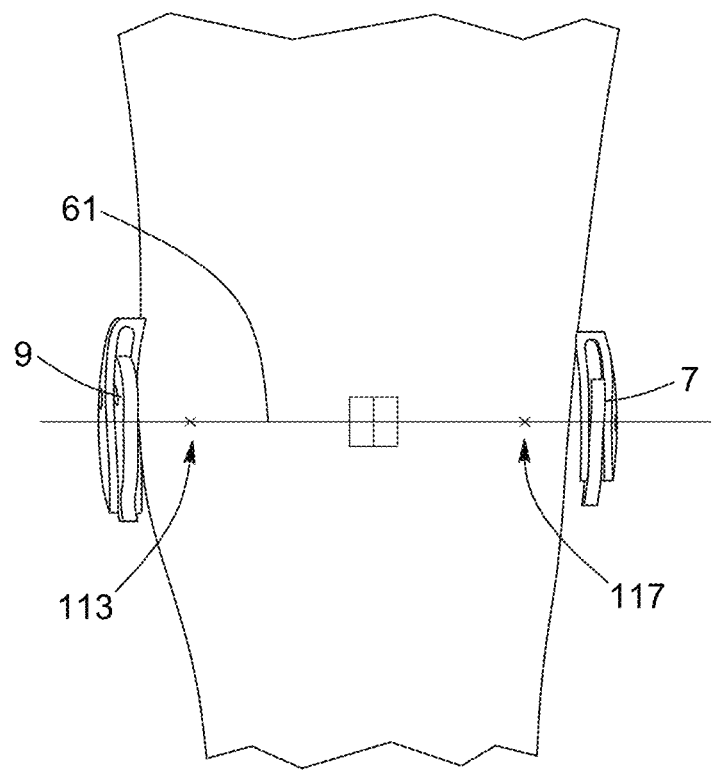
FIG. 22 illustrates medial and lateral hinges positioned on the medial and lateral femoral condyles of a wearer's knee.

As can be further appreciated, as shown in FIG. 22, the hinges 7, 9 and their corresponding pivots can be configured such that the pivot axis 61 extends through the medial and lateral condyles throughout a full articulation of the wearer's knee. For example, the medial hinge 7 can be positioned in alignment with the medial condyle 117 at full knee extension, and the lateral hinge 9 can be positioned in alignment with the lateral condyle 113 at full knee extension, and the hinges 7, 9 can be configured with a pivot axis 61 which follows the helicoidal axis of movement of the knee such that they remain in alignment with their respective condyle throughout flexion and subsequent extension (i.e. through the full articulation). For example, the pivot axis 61 can be configured to correspond to the transepicondilar axis of the wearer's knee. As mentioned above, each of the hinges 7, 9 can be configured to move independently from one another about their respective pivots. As such, each hinge 7, 9 can be configured to separately follow the movement of its respective condyle. As shown in FIG. 4, the medial hinge 7 can be configured with a first pivot which allows it to follow its corresponding medial anatomical joint 117 (medial condyle) through a first arcuate path 119, and the lateral hinge 9 can be configured with a second pivot which allows it to follow its corresponding lateral anatomical joint 113 (lateral condyle) through a second arcuate path 115 which is different than the first arcuate path. The movements of the medial 7 and lateral 9 hinges can be synchronized with movements of the wearer's medial and lateral condyles, such that the pivot axis of the orthosis 1 is synchronized with the helicoidal axis of movements of the wearer's knee.

Figure 20B:
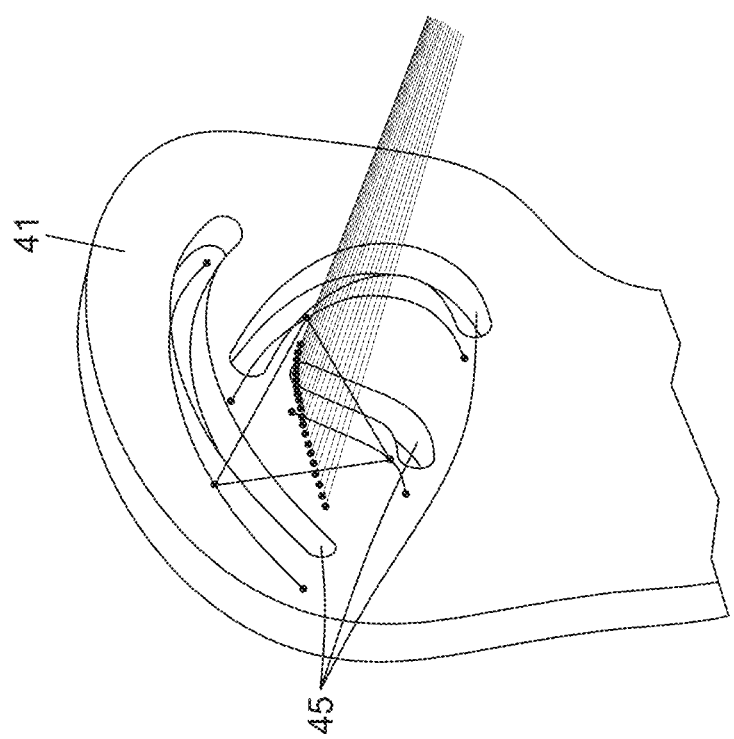
FIG. 20B is a perspective view of the interior surface of the tibial section of FIG. 20A.
Figure 20A:
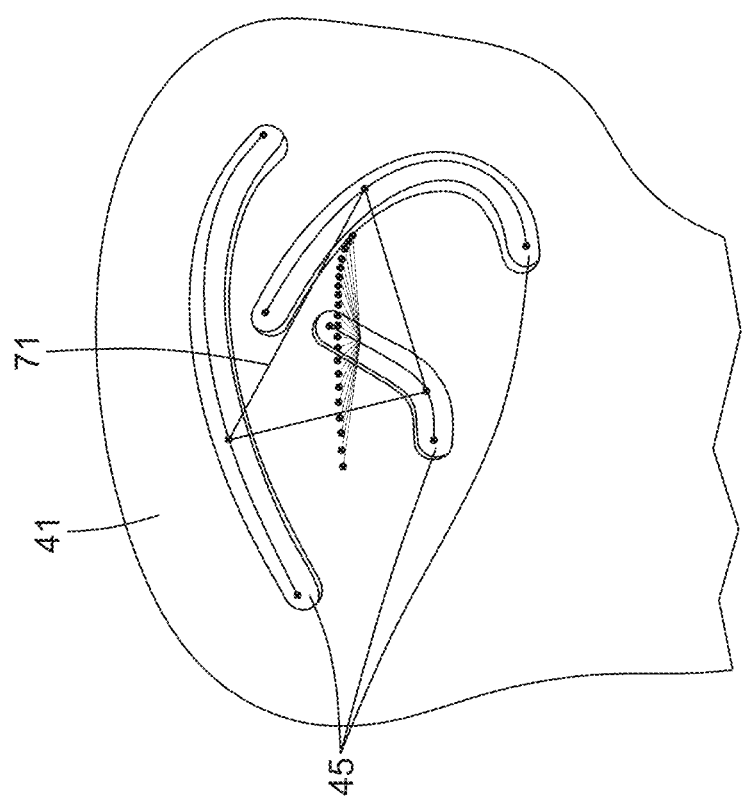
FIG. 20A is an elevation view of the interior surface of the tibial section of an orthosis hinge, showing an extremity of the knee helicoidal axis of rotation, and configuration of grooves to follow the same, according to an embodiment.

As can be appreciated, the helicoidal axis of rotation of the knee can be used to determine the shape of the guiding channels in the shells to define a pivot axis 61 which corresponds to natural knee movement. With reference to FIGS. 20A and 20B, three guiding elements run across the shells 41 of the medial and lateral femoral hinges, in the present embodiment corresponding to the guiding channels 45 guiding corresponding pins fixed relative to the shells 21 of the medial and lateral tibial hinges. The guiding elements form a triangle 71 whose center can correspond to an extremity 61a, 61b, of the pivot axis 61. In this configuration, the resulting movement of the triangle 71 formed by the three guiding elements corresponds to the displacement of each extremity 61a, 61b of the pivot axis 61. In this fashion, a desired displacement of the triangle 71 can be predetermined, and the displacement of the triangle vertices can be used to define the grooves in the medial and lateral tibial hinges. As can be appreciated, the medial hinge 7 can be configured based on a displacement of its triangle 71 that follows a path of the medial extremity of the helicoidal axis of rotation of the wearer's knee. Similarly, the lateral hinge 9 can be configured based on a displacement of its triangle 71 that follows a path of the lateral extremity of the helicoidal axis of rotation of the wearer's knee. In this fashion, the medial hinge will be configured to move about a first pivot which corresponds to a medial extremity of the helicoidal axis of rotation of the wearer's knee, whereas the lateral hinge will be configured to move about a second pivot corresponding to a lateral extremity of the helicoidal axis of rotation of the wearer's knee.

Figure 21:
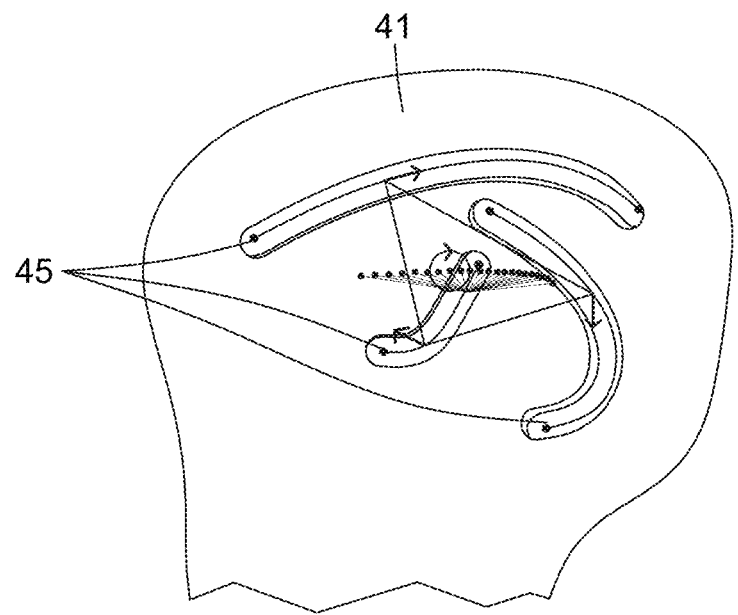
FIG. 21 is an elevation view of the interior surface of the tibial section of FIG. 20A, showing the angles formed by the tangent of the initial direction of the grooves at the initiation of knee flexion.

The initial organization of the triangle formed by the guiding elements can be established while considering the following elements: to trace grooves that do not cross each other; to obtain a triangle with the largest possible size to avoid concentration of constraints on a pin while obtaining a shell with the smallest possible size; to avoid blockages of the hinges during movement; and to reduce the curves of the grooves to ensure a fluid movement of the pins in the grooves and avoid blocking of the pins in the grooves. For example, and with reference to FIG. 21, the guiding elements can be configured such that at the initial position of the pivot axis in full extension (i.e. at the initiation of flexion), the angle formed by the tangent of the initial direction of the guiding elements be as close as possible to 90° in reference to the center of the triangle. This can help to avoid blockage of the hinge during knee movement.

In addition to the configuration of the hinges described above, it is appreciated that the orthosis 1 can be configured to help realign a wearer's leg in order to further help guide healthy and/or natural knee movement. In the present embodiment, and with reference to FIG. 23, the femoral 3 and tibial 5 section are configured to apply force at strategic areas or regions along the wearer's leg in order to change an alignment of the wearer's tibia (i.e. shin) in relation to the femur (i.e. thigh) in the frontal plan. In this fashion, the alignment of the wearer's leg can be corrected so as to correspond to a healthy alignment and/or the alignment can be adjusted, for example to discharge a worn area of the wearer's knee (i.e. move the contact points to an area that is less worn and/or redistribute forces in the wearer's knee). In some embodiments, as will be described in more detail hereinbelow, the orthosis 1 can be configured to realign the leg of an osteoarthritic patient such that the medial-shifted tibiofemoral contact points are displaced laterally to correspond to contact points of a healthy patient throughout flexion and extension.

Figure 23:
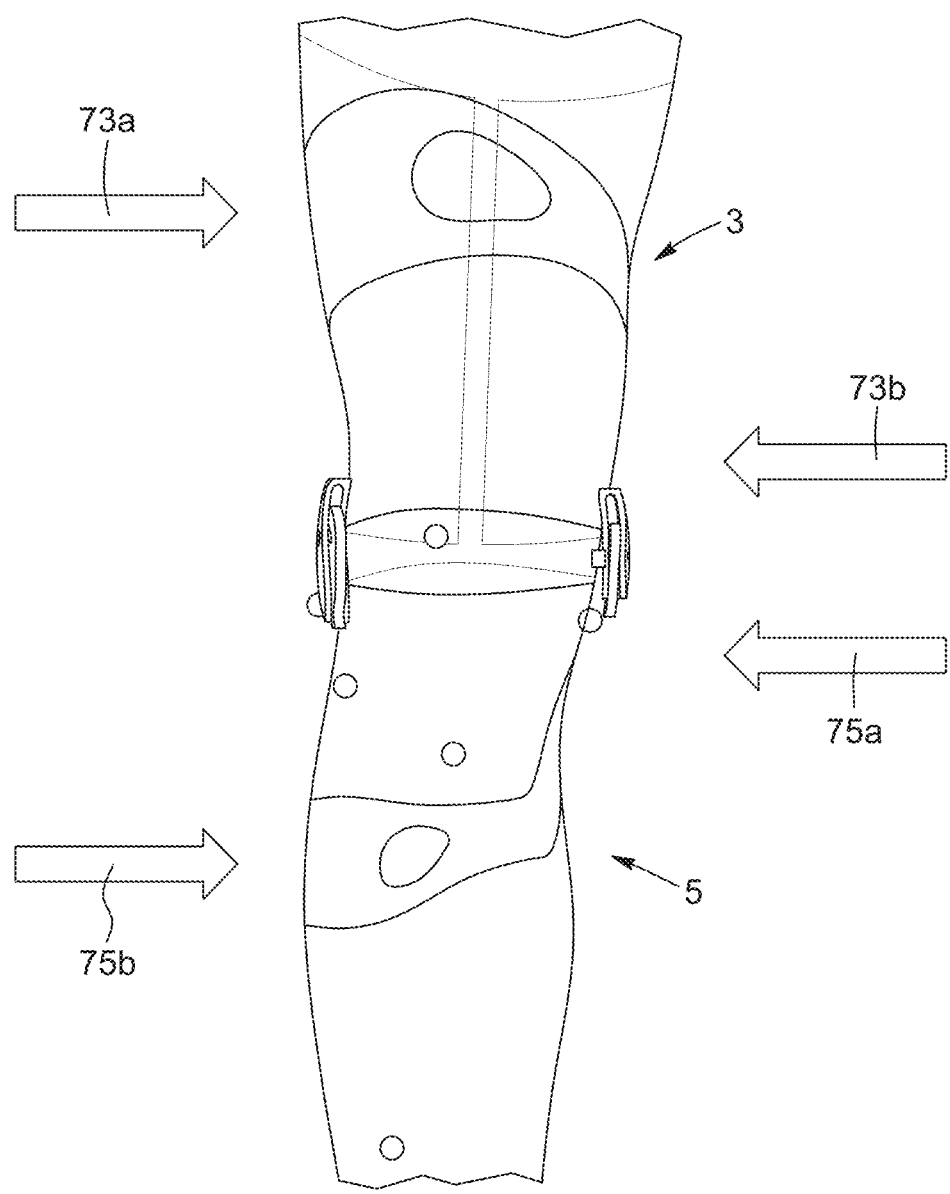
FIG. 23 is a schematic illustrating areas of force application used to realign a wearer's tibia in relation to the wearer's femur in the frontal plane.

In the present embodiment, as shown in FIG. 23 the femoral section 3 is configured to apply two areas of force in relation to the wearer's thigh, namely a first area of force 73a on a proximal area of the femoral section 3, and a second area of force 73b on a distal area of the femoral section 3, for example proximate to the hinge. Similarly, the tibial section 5 is configured to apply two areas of force in relation to the wearer's shin, namely a first area of force 75a on a proximal area of the tibial section 5, for example proximate to the hinge, and a second area of force 75b on a distal area of the tibial section. As can be appreciated, these areas of force can be applied by shaping the cuffs 13, 23, support members 17, 27 and/or hinges 7, 9 to apply pressure to a desired area of the wearer's leg and/or by increasing or decreasing rigidity of the cuffs 13, 23, support members 17, 27 and/or hinges 7, 9 at predetermined areas to prevent or permit deformation thereof during movement of the wearer's leg. As can be further appreciated, the number and location of the areas of pressure/force can vary depending on how the wearer's leg needs to be realigned. For example, in the present embodiment, forces 73a and 75b are applied on a lateral side of the wearer's leg, whereas forces 73b and 75a are applied on a medial side of the wearer's leg, but it is appreciated that the positions of force application can be inversed. Similarly, in the present embodiment, forces 73b and 75a are applied in an area adjacent to the hinges 7, 9, for example via support members 17a, 17b. In this configuration, the forces are not applied to the wearer's condyles, but instead on areas proximal/distal thereto on the wearer's tibia and femur.

It is appreciated that in other embodiments, forces can be applied in different areas, for example to realign the leg in the sagittal and/or transverse planes. As can be further appreciated, the positions of the areas of force being applied can be implicit to the orthosis design. For example, the orthosis can be designed to conform to a desired alignment of the wearer's leg and corresponding movement thereof, rather than to the actual alignment of the wearer's leg. In this fashion, when the orthosis is worn, the rigidity of the orthosis will naturally encourage the wearer's leg to realign and move as designed.

It is further appreciated that more or fewer areas of pressure/force application can be provided. For example, although in the present embodiment there are a total of four areas of force applied, three areas of force can be applied to encourage realignment of the wearer's leg in other embodiments. For example, depending on the required realignment, forces 73b, 75a can be applied as a single force to one of the wearer's condyles via hinges 7 or 9, with forces 73a and 75b acting as counterforces thereto to define a three-point leverage system. As can be appreciated, this can assist in correcting/adjusting an alignment angle of the wearer's tibia and femur, for example to unload the patient's knee (i.e. redistribute forces from one side of the joint to another) by adjusting the angle of the femur relative to the tibia. Realigning the femur and tibia in this fashion can help correct valgus and varus deformations of the knee. For example, in the case of a valgus deformation, forces 73b, 75a can be applied to the wearer's medial condyle via medial hinge 7, with counterforces 73a and 75b being applied on the lateral side of the wearer's femur and tibia. Similarly, in the case of a varus deformation, forces 73b, 75a can be applied to the wearer's lateral condyle via lateral hinge 9, with counterforces 73a and 75b being applied on the medial side of the wearer's femur and tibia.

Figure 28:
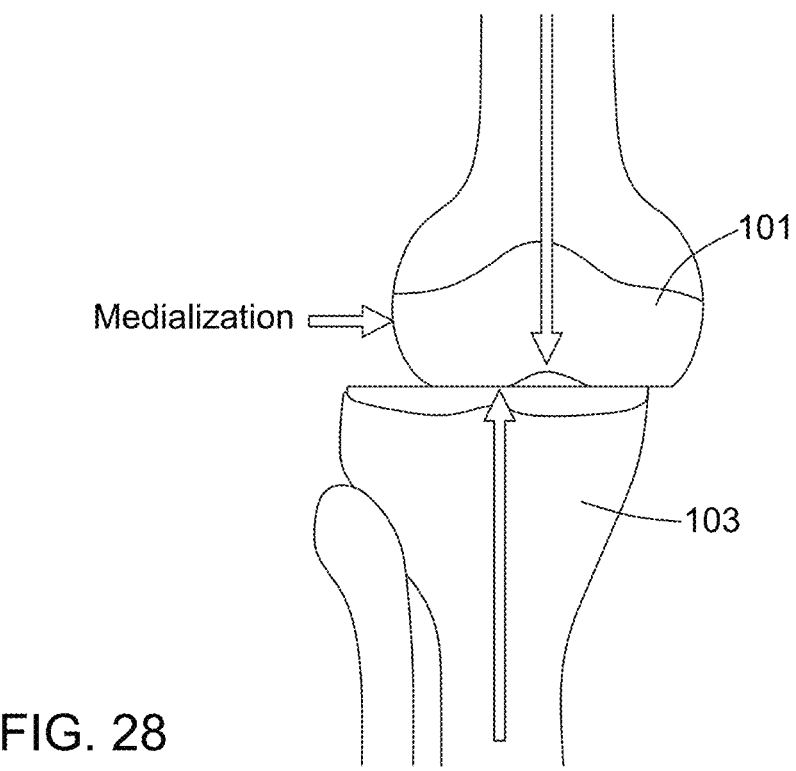
FIG. 28 is a schematic illustrating medialization of the femur in osteoarthritic patients.

In some embodiments, the areas of pressure/force application can be configured to correct medialization of the femur relative to the tibia, for example in osteoarthritic patients. As shown schematically in FIG. 28, in osteoarthritic patients (both in valgus and varus cases), the patient's femur 101 medializes (i.e. translates in the medial direction) on the tibia 103, thus causing a medial shift in the tibiofemoral contact points through flexion and extension, as illustrated in FIG. 11. The orthosis 1 can be designed to correct this by applying a lateral translation on the femur in order to correct for medialization and bring the tibiofemoral contact points of an osteoarthritic patient closer to what they were originally without osteoarthrosis. As can be appreciated, by applying forces and counterforces at particular areas, the translation of the femur relative to the tibia can be applied in addition to adjusting an angle of the tibia relative to the femur to unload the knee and/or correct varus/valgus deformities.

Figures 28A, 28B:
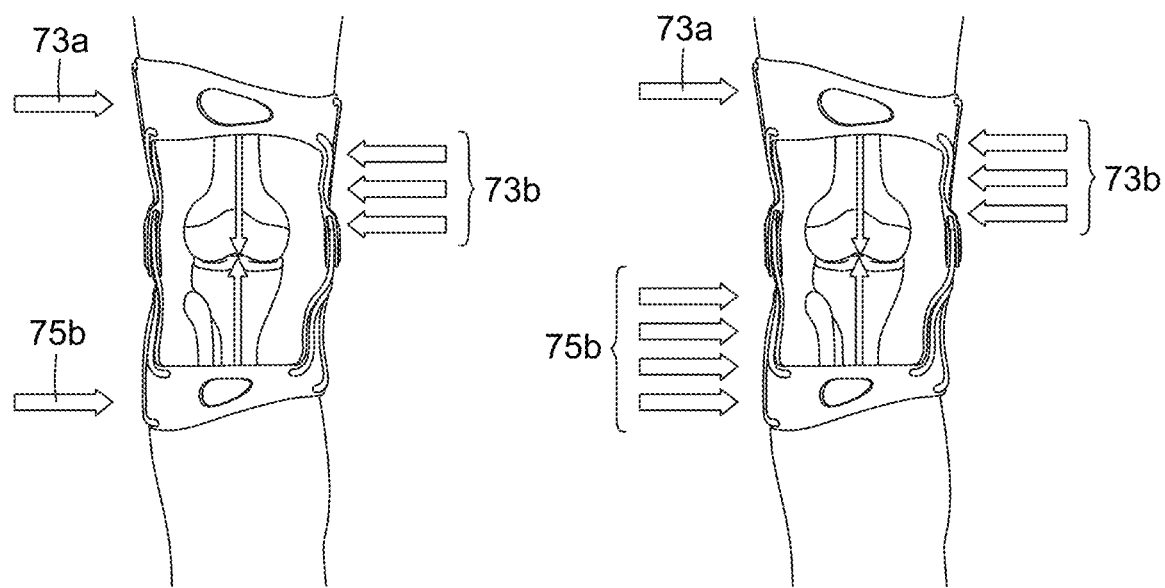
FIG. 28A is a schematic illustrating areas of force application used to correct medialization of the femur along with a valgus deformity.
FIG. 28B is a schematic illustrating areas of force application used to correct medialization of the femur along with a varus deformity.

With reference to FIG. 28A, an exemplary configuration of force application is shown according to an embodiment for correcting medialization and valgus deformation. In the illustrated embodiment, a first area of force 73a is applied on the lateral side of the wearer's femur via a proximal area of femoral section 3, for example via the femoral cuff. A second area of force 73b is applied along the medial side of the wearer's femur via the medial side of femoral section 3, for example via medial support member. A third area of force 75b is applied on the lateral side of the wearer's tibia via a distal area of tibial section 5, for example via the tibial cuff. As can be appreciated, this configuration of forces can apply a lateral translation of the femur to correct medialization, while adjusting an angle of the femur relative to the tibia to correct the valgus deformation and unload the knee. In the present configuration, forces 73b and 75b act as anti-valgus forces, whereas force 73a acts as a counter force. As can be appreciated, force 73b can be configured to be greater than forces 73a, 75b, and can also be configured to extend over a longer area along the wearer's leg. For example, forces 73a and 75b can be confined to the femoral and tibial cuffs, whereas force 73b can extend along a longer area of medial support member and can further extend to apply force on the wearer's medial condyle via medial hinge 7.

With reference to FIG. 28B, an exemplary configuration of force application is shown according to an embodiment for correcting medialization and varus deformation. In the illustrated embodiment, a first area of force 73a is applied on the lateral side of the wearer's femur via a proximal area of femoral section 3, for example via the femoral cuff. A second area of force 73b is applied along the medial side of the wearer's femur via the medial side of femoral section 3, for example via medial support member. A third area of force 75b is applied on the lateral side of the wearer's tibia via tibial section 5. As can be appreciated, this configuration of forces can apply a lateral translation of the femur to correct medialization, while adjusting an angle of the femur relative to the tibia to correct the varus deformation and unload the knee. In the present configuration, force 73b acts as anti-valgus force, force 75b acts as an anti-varus force, and force 73a acts as a counter force. As can be appreciated, force 73b can be configured to be greater than forces 73a, and can also be configured to extend over a longer area along the wearer's leg. For example, force 73a can be confined to the femoral cuff, whereas force 73b can extend along a longer area of medial support member and can further extend to apply force on the wearer's medial condyle via medial hinge 7. As can be further appreciated, force 75b can be configured to be greater than force 73b, and can also be configured to extend over a longer area along the wearer's leg. For example, force 75b can be configured to extend along the lateral support member and can further extend to apply force via the tibial cuff. In some embodiments, force 75b can further extend to apply force on the wearer's lateral condyle via lateral hinge 9.

As described above, the knee orthosis can be tailored to conform to the specific anatomy of a wearer. More specifically, the shape and contour of femoral and tibial sections can be configured to conform to the actual surface contours of the wearer's leg. Similarly, the hinges can be configured according to the specific anatomy of the wearer's leg, such that the orthosis guides the knee to move in a natural and healthy way, following a desired helicoidal axis of rotation as described above.

With reference to FIG. 26, an exemplary process for bespoke knee orthosis manufacturing is shown. Broadly described, the process involves the steps of a) scanning the wearer's leg to obtain a 3D model thereof; b) modelling a bespoke knee orthosis using the 3D model; c) manufacturing the individual components of the bespoke knee orthosis; and d) assembling the individual components to form the completed knee orthosis.

In more detail now, the step of scanning the wearer's leg can be achieved using known imaging/scanning techniques to obtain a 3D model of the shape of the wearer's leg. For example, the wearer's leg can be digitized using a scanner. During digitization, the wearer's leg can be covered with a tube made of extensible fabric to contain soft structures. In generating the 3D model, landmarks can be identified thereon in order to assist in positioning and designing the knee orthosis. For example, as shown in FIGS. 27A to 27D, the landmarks can include, among others: tubercle of adductor magnus muscle 79a, middle of external tibial plateau 79b, half of the superior portion of the thigh 79c, half of the leg at the apex of the calf muscle 79d, tibial tuberosity 79e, antero-medial tibial plateau 79f, antero-lateral tibial plateau 79g, half of the superior portion of the thigh 79h, half of the inferior portion of the thigh at the distal portion of the femur and superior to the patella 79i, half of the leg at the apex of the calf muscle 79j, middle of popliteal fossa 79k, half of the superior portion of the thigh 79l, and half of the leg at the apex of the calf muscle 79m. As can be appreciated, these landmarks can be located by positioning markers on the wearer's leg prior to imaging/scanning (for example by positioning markers on the extensible tube) and/or can be positioned virtually after obtaining the 3D model.

The step of modelling the bespoke knee orthosis can include a number of sub-steps. For example, in an embodiment, a first sub-step can comprise importing the generated 3D model of the wearer's leg, and virtually adjusting alignment of the wearer's thigh and shin in the frontal plane, for example to correspond to an alignment of a healthy natural knee, as described above, and/or to discharge or redistribute forces in the knee. As can be appreciated, the alignment can be adjusted according to the patient's needs, and will ultimately determine how areas of force will be applied to the wearer's leg via the orthosis. For example, in a non-osteoarthritic patient, the 3D model can be adjusted to adjust an angle of the femur relative to the tibia to correct valgus/varus deformities. In an osteoarthritic patient, the 3D model can be adjusted to displace/translate the femur laterally to correct for medialization of the femur relative to the tibia. The 3D model can further be adjusted to adjust an angle of the femur relative to the tibia to correct valgus/varus deformities. Once adjusted, the realigned 3D model can be used to design and position the hinges and cuffs.

As illustrated in FIG. 25A, a second sub-step can comprise using the 3D model to virtually position the medial 7 and lateral 9 hinges on their corresponding medial and lateral condyles on the 3D model. Positioning of the hinges can be assisted, for example, using the landmarks identified during knee digitization. In some embodiments, interior surfaces of the hinges can be adapted to conform to the external contours of the wearer's leg in the location where the hinges are positioned. Moreover, the size of medial 7 and lateral 9 hinges and their corresponding shells can be selected to correspond to a size of the wearer's medial and lateral condyles.

Next, as illustrated in FIG. 25B, a third sub-step can comprise virtually modelling the femoral 13 and tibial 33 cuffs on the external surfaces of the wearer's thigh and shin. The cuffs 13, 33 and support members extending therefrom can, for example, be shaped to conform to the external surfaces of the wearer's leg, including any deformations present on the wearer's skin. It is appreciated, however that other parameters of the cuffs and/or support members can be adjusted as well, such as: thickness of the cuffs, position or shape of rigidity structures (such as position or shape of reinforcements or ribs on the cuffs/support members, and/or number, form and/or position of openings on the cuffs/support members), number and position of straps, etc. As can be appreciated, the modelling of cuffs and/or the adjustments thereof can be achieved using a specialized software.

Next, as illustrated in FIG. 25C, a fourth sub-step can comprise integrating the cuffs with their respective hinges. In this step, the femoral cuff and femoral hinge can be formed as a single piece, namely the femoral section 3. Similarly, the tibial cuff and tibial hinge can be formed as a single piece, namely the tibial section 5. The two pieces can be articulated into one another, and a 3D model can be generated for each of the pieces 3, 5, for example in the STL or STP formats. This can be achieved, for example, using a specialized software.

After the orthosis has been modelled, its individual components can be manufactured. As can be appreciated, the 3D models of the femoral 3 and tibial 5 sections can be fabricated using additive manufacturing techniques, such as 3D printing. Fabrication can be realized using any suitable material, which allows proper elasticity and rigidity properties in order to adapt itself to the wearer's limb during movement, such as deformation of soft structures during walking. For example, the pieces can be made from plastic. Diverse colors can be applied on the pieces according to wearer's preferences. Although in the present embodiment the femoral 3 and tibial 5 section are manufactured as single pieces, it is appreciated that in some embodiments, different components of the femoral and/or tibial 5 sections can be manufactured separately and subsequently assembled. For example, the hinge of femoral 3 and/or tibial 5 sections can be manufactured from a first rigid material, separate from the cuffs. The cuffs can be manufactured separately, and assembled to the hinge, for example via fasteners, adhesives, welding/fusing, etc.

Finally, after the pieces of the orthosis have been manufactured, they can be assembled. As can be appreciated, once the manufactured femoral 3 and tibial 5 pieces are received, they can be refined (if necessary), secured and provided with additional components to form the completed orthosis 1 as illustrated in FIGS. 25D and 24. More specifically, the grooves and/or surfaces of the tibial and/or femoral hinges can be polished to allow smooth gliding of the pins and/or abutting surfaces. In the present embodiment, the hinges can be assembled by inserting the shell of the tibial hinge between the shells of the femoral hinge, and pins can be inserted in the femoral hinges and go through the respective groove on the tibial hinge. The pins can then be screwed and secured at an opposite end by a nut to allow easy sliding in the grooves. It is appreciated, however, that other assembly steps can apply depending on the guiding mechanism used in other embodiments. In some embodiments, buckles and straps 77 can be added (for example, secured to specific areas predefined in the femoral and/or tibial sections) and adjusted in reference to the size of patient's thigh and shin. Finally, a cushioned liner can be added to interior surfaces of the femoral 3 and/or tibial 5 sections complete the fabrication of the orthosis 1.

In summary, in the present disclosure, knee movement measures are achieved by imaging. Knee movement is represented in references to three planes and considered in six degrees of freedom. The articulations are positioned virtually according to anatomic landmarks, and other orthosis parts are connected thereto to form a single integral component by additive manufacture, for example without recourse to plaster material.

In the described embodiments, the knee bones remain in the proper axis. As described above, knee movement defines a helicoidal axis and that knee movement is different between its internal and external femoral condyles. Embodiments of the orthosis can thus be made with an axial rotation system, i.e. in addition to the sagittal plane. The orthosis can take into account the greater long-term wear of the internal cartilage relative to the external cartilage. This can create an orthosis induced translation and can clear the medial condyle.

In the described embodiments, there are four areas of application of force: two areas on the tibia and two on the femur, for realignment of the lower limb segments in reference to the frontal plane. Translation and rotation of the tibia can enable modification of articulation in the frontal plane, to address knee osteoarthritis. Corrective translation of the tibia can thus be achieved.

The orthosis can be assembled as a unit, but can comprise three brass screws which engage three arcuate grooves of the orthosis. Three-dimensional measurement of knee movement can be achieved to obtained representation of instantaneous axis of normal knee movement in orthosis articulations. The two femoral condyles come to bear against the tibial plateau and have different size, geometry and function. Thus it can be necessary to take into account the differential knee movement at the two condyles. Flexion and extension, abduction and adduction, as well as internal and external rotation are achieved.

Embodiments of the orthosis described herein can be characterized by the femoral roll back (sliding motion of external condyle in reference to medial condyle) and screw home (pivotal action of lateral condyle around the medial condyle) mechanisms during knee flexion and extension, which is enabled by the asymmetry of the two femoral condyles. The orthosis has a concavity, which eliminates need for a connector mechanism used in prior art orthoses.

In some embodiments, lower limb repositioning can be achieved to correct misalignment of the leg relative to the thigh, mainly in the frontal plane (genu varum/valgum conditions) and sagittal (genu flexum/recurvatum conditions), since this misalignment is often linked to an excessive wear on certain parts of the knee articulation and/or to a non-efficient function in terms of movement in space and of transfer of forces between the two segments. Embodiments of the orthosis described herein can enable repositioning of these segments in a virtual way, via a custom made software and anatomic landmarks. This repositioning can be substantially less invasive and less expensive than prior art plaster techniques.

In some embodiments, positioning of mechanisms can be enabled by the geometric relations between the anatomic landmarks, which allow not only to realign the shin relative to the thigh, but also to define the position of the internal and external condyles of the knee on which are centered the medial and lateral articulations of the orthosis. The positioning of the orthosis articulations can then enable determination of the positioning of the rotational axis path of the knee. This can be done automatically by software modelling the orthosis, thus increasing reliability of the manufacturing method and providing normalisation of knee movement.

In some embodiments, the embrace can comprise contacting areas between the orthosis and the wearer's body surface and can consist of the tibial and femoral cuffs. Custom made software can allow defining and positioning of the cuffs, by virtually sliding same on the digital shape of the lower limb. This in turn can allow a personalized shape for the cuffs and takes into account individual features (such as contour, protuberances, discrepancies on the skin surface, etc.). When the cuff design is finished, it can become automatically linked to the articulations with the above-noted software. This step can determine the transfer of forces between the cuffs or frame of the orthosis and its articulations.

In some embodiments, the two cuff components (tibia and femoral) can be forwarded to an additive manufacturing service supplier for fabrication. Upon receiving same, the components can be assembled at the level of the articulations and the finishing steps are completed, namely, the addition of buckles, straps and cushioned liner.

The invention claimed is:

1. A knee orthosis comprising:
a femoral section comprising a femoral cuff and a femoral hinge integrally formed as part of a single piece; and
a tibial section comprising a tibial cuff and a tibial hinge, said tibial cuff and tibial hinge being integrally formed as part of a single piece,
the femoral hinge and the tibial hinge being pivotally engaged to define an orthosis articulation allowing the femoral section and the tibial section to pivot relative to one another about a pivot axis, said pivot axis being configured to move in a sagittal plane, a frontal plane and a transverse plane, as the femoral and tibial sections are pivoted relative to one another about the articulation.

2. The knee orthosis according to claim 1, wherein the femoral and tibial hinges each respectively comprise spherical shells engaged with one another, the spherical shells being pivotable relative to one another to define the orthosis articulation.

3. The knee orthosis according to claim 2, wherein the femoral hinge comprises a pair of parallel shells spaced apart from one another, and the shell of the tibial hinge is positioned in a space between the pair of parallel shells.

4. The knee orthosis according to claim 3, wherein the femoral and tibial hinges each comprise medial shells together defining a medial hinge, and lateral shells together defining a lateral hinge.

5. The knee orthosis according to claim 4, wherein the medial hinge is positioned to align with a medial femoral condyle, and the lateral hinge is positioned to align with a lateral femoral condyle, when the orthosis is worn by a wearer.

6. The knee orthosis according to claim 5, wherein a hinge axis of the medial hinge is configured to rotate about a first pivot following an instantaneous movement axis of the medial condyle, and a hinge axis of the lateral hinge is configured to rotate about a second pivot following an instantaneous movement axis of the lateral femoral condyle, during flexion and extension of the wearer's knee.

7. The knee orthosis according to claim 5, wherein the medial hinge is configured to guide a displacement of a medial extremity of the pivot axis along a first arcuate path, and the lateral hinge is configured to guide a displacement of a lateral extremity of the pivot axis along a second arcuate path, during flexion and extension of the wearer's knee.

8. The knee orthosis according to claim 4, wherein the medial shells are shaped as an arc of a sphere having a first geometric center, and the laterals shells are shaped as an arc of a sphere having a second geometric center which does not coincide with the first geometric center.

9. The knee orthosis according to claim 8, wherein the medial and lateral shells are configured with geometric centers which move as the femoral and tibial sections are pivoted relative to one another, the geometric centers of the medial and lateral shells intersecting along a common pivot axis having a center which is constrained to a common sagittal plane throughout a full articulation of the orthosis.

10. The knee orthosis according to claim 4, wherein the medial shells of the femoral and tibial hinges are shaped as an arc of a sphere having a first diameter, and the lateral shells of the femoral and tibial hinges are shaped as an arc of a sphere having a second diameter different than the first diameter.

11. The knee orthosis according to claim 2, wherein at least one of the shells in the femoral and tibial hinges comprises grooves shaped to engage with corresponding pins and guide the same along a predetermined path.

12. The knee orthosis according to claim 11, wherein the shells in the femoral and tibial hinges comprise three grooves shaped to engage with and guide movement of three corresponding pins, the three pins being arranged in a triangular formation and having a center corresponding to an extremity of the pivot axis.

13. The knee orthosis according to claim 12, wherein the three grooves are arranged to cause a displacement of the center of the triangle along an arcuate path as the pins move along their predetermined paths in the three grooves.

14. The knee orthosis according to claim 11, wherein at least one pin is integrally formed as part of the shell of the femoral hinge or the tibial hinge.

15. The knee orthosis according to claim 14, wherein the at least one pin extends from the interior surface of the shell of the femoral hinge or the tibial hinge.

16. The knee orthosis according to claim 3, wherein each of the spherical shells of the pair of parallel shells are shaped as an arc of a sphere of constant diameter.

17. The knee orthosis according to claim 11, wherein the shell of the femoral hinge comprises at least one groove formed therein for guiding a corresponding pin fixed relative to the shell of the tibial hinge, and the shell of the tibial hinge comprises at least one groove formed therein for guiding a corresponding pin fixed relative to the shell of the medial hinge.

18. The knee orthosis according to claim 11, wherein at least one of the femoral and tibial hinges comprises a pair of shells spaced apart from one another, further wherein at least one pin extends between the pair of shells and is fixed relative thereto.

19. The knee orthosis according to claim 11, wherein the grooves comprise apertures opening on an exterior side and on an interior side of the shell.

20. The knee orthosis according to claim 1, wherein the femoral and tibial cuffs each comprise medial and lateral support members extending along medial and lateral sides of the knee orthosis.

21. The knee orthosis according to claim 20, further comprising a plurality of straps extending between the medial and lateral support members on a posterior side of the knee orthosis.

22. The knee orthosis according to claim 20, further comprising at least one strap extending between the medial and lateral support members on an anterior side of the knee orthosis.

23. The knee orthosis according to claim 2, wherein the shells are sized and/or shaped to conform to a specific anatomy of the wearer.

24. The knee orthosis according to claim 1, wherein the femoral section is configured to apply two or three areas of force to the wearer's femur, and wherein the tibial section is configured to apply two or three areas of force to the wearer's tibia, to realign the wearer's femur with respect to the wearer's tibia in a frontal plane.

25. The knee orthosis according to claim 24, wherein the femoral and tibial sections are each configured to apply a first area of force on a lateral side of the wearer's leg and a second area of force on a medial side of the wearer's leg.

26. The knee orthosis according to claim 24, wherein the femoral and tibial sections are each configured to apply a first area of force via a proximal section of the femoral or tibial cuff, and a second area of force via a distal section of the femoral or tibial cuff.

27. The knee orthosis according to claim 1, wherein the pivot axis of the orthosis articulation is configured to follow an anatomical axis of a wearer's knee along five or six degrees of freedom.

28. The knee orthosis according to claim 1, wherein the femoral and tibial hinges are configured to allow the pivot axis to move helicoidally as the femoral and tibial sections are pivoted relative to one another about the articulation.

29. The knee orthosis according to claim 1, wherein the femoral and tibial hinges are configured to allow the pivot axis to move while accounting for femoral roll back and screw home mechanisms during flexion and extension of the wearer's knee.

30. The knee orthosis according to claim 1, wherein the femoral and tibial cuffs are sized and/or shaped to conform to a specific anatomy of the wearer.

31. The knee orthosis according to claim 1, wherein the femoral and tibial sections are configured to apply forces to encourage a lateral translation of the wearer's femur relative to the tibia throughout the articulation of the orthosis, to correct for medialization.

32. The knee orthosis according to claim 1, wherein the femoral and tibial sections are configured to apply forces to adjust an angle of the femur relative to the tibia throughout the articulation of the orthosis, to correct for valgus or varus deformities.

* * * * *